(12) United States Patent
Raboisson et al.

(10) Patent No.: US 9,987,277 B2
(45) Date of Patent: Jun. 5, 2018

(54) CARBOXAMIDE 4-[(4-PYRIDYL)AMINO] PRYIMIDINES FOR THE TREATMENT OF HEPATITIS C

(75) Inventors: Pierre Jean-Marie Bernard Raboisson, Rosieres (BE); Oliver Lenz, Sint-Katelijne-Waver (BE); Tse-I Lin, Mechelen (BE); Kenneth Simmen, Tervuren (BE)

(73) Assignee: Janssen Sciences Ireland UC, Little Island, Co. Cork (IE)

(*) Notice: Subject to any disclaimer, the term of this patent is extended or adjusted under 35 U.S.C. 154(b) by 1407 days.

(21) Appl. No.: 12/443,190

(22) PCT Filed: Oct. 4, 2007

(86) PCT No.: PCT/EP2007/060539
§ 371 (c)(1),
(2), (4) Date: Mar. 27, 2009

(87) PCT Pub. No.: WO2008/040778
PCT Pub. Date: Apr. 10, 2008

(65) Prior Publication Data
US 2009/0247523 A1    Oct. 1, 2009

(30) Foreign Application Priority Data
Oct. 4, 2006   (EP) .................................... 06121756

(51) Int. Cl.
*A61K 31/21* (2006.01)
*A61K 31/506* (2006.01)
*A61K 31/535* (2006.01)

(52) U.S. Cl.
CPC .......... *A61K 31/506* (2013.01); *A61K 31/535* (2013.01)

(58) Field of Classification Search
CPC .................................................... A61K 31/505
USPC ........................................................ 514/256
See application file for complete search history.

(56) References Cited

U.S. PATENT DOCUMENTS

| | | |
|---|---|---|
| 5,807,876 A | 9/1998 | Armistead et al. |
| 6,054,472 A | 4/2000 | Armistead et al. |
| 6,344,465 B1 | 2/2002 | Armistead et al. |
| 6,476,031 B1 | 11/2002 | Chakravarty et al. |
| 6,498,178 B2 | 12/2002 | Stamos et al. |
| 2004/0132159 A1 | 7/2004 | Zhong et al. |
| 2004/0132730 A1 | 7/2004 | Axon et al. |
| 2005/0004143 A1 | 1/2005 | Dugar et al. |
| 2006/0281763 A1* | 12/2006 | Axon et al. .................. 514/256 |

FOREIGN PATENT DOCUMENTS

| | | |
|---|---|---|
| WO | WO 97/40028 A1 | 10/1997 |
| WO | WO 98/40381 A1 | 9/1998 |
| WO | WO 00/563331 A1 | 9/2000 |
| WO | WO 01/47921 A1 | 7/2001 |
| WO | WO 2003/042207 | 5/2003 |
| WO | WO 2003/042211 | 5/2003 |
| WO | WO 03/084953 A1 | 10/2003 |
| WO | WO 04/024159 A1 | 3/2004 |
| WO | WO 05/117885 A1 | 3/2004 |
| WO | WO2004/078207 A1 * | 9/2004 |
| WO | WO 2004/087056 | 10/2004 |
| WO | WO 2006/100310 | 9/2006 |
| WO | WO 06/105222 A2 | 10/2006 |

OTHER PUBLICATIONS

Sarbah et al. "Risk factors for hepatocellular carcinoma in patients with cirrhosis," Digestive Diseases and Sciences, 2004, vol. 49, No. 5, pp. 850-853.*
"National Institute of Health Consensus Development Conference Statement: management of Hepatitis C 2002", Hepatology vol. 36, No. 5, Suppl. 1 (2002).
Krieger, N., et al. "Enhancement of Hepatitis C Virus RNA Replication by Cell Culture—Adaptive Mutations", Journal of Virology, vol. 75, No. 10 p. 464 (2001).
Lohmann, V., et al. "Replication of Subgenomic Hepatitis C Virus RNAs in a Hepatoma Cell Line", Science vol. 285. 285 p. 110 (1999).
Raboisson, P., et al. "Evaluation of the Anti-Hepatitis C Virus Effect of Novel Potent, Selective, and Orally Bioavailable JNK and VEGFR Kinase Inhibitors", Bioorganic Medicinal Chemistry Letters, vol. 17, No. 7, p. 1843 (2007).

* cited by examiner

*Primary Examiner* — Shengjun Wang
(74) *Attorney, Agent, or Firm* — Baker & Hostetler LLP

(57) ABSTRACT

The present invention relates to the use of carboxamide 4-[(4-pyridyl)amino]-pyrimidines as inhibitors of HCV replication as well as their use in pharmaceutical compositions aimed to treat or combat HCV infections.

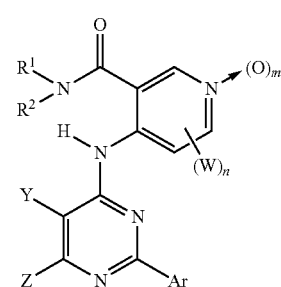

27 Claims, No Drawings

CARBOXAMIDE 4-[(4-PYRIDYL)AMINO] PRYIMIDINES FOR THE TREATMENT OF HEPATITIS C

CROSS-REFERENCE TO RELATED APPLICATIONS

This application claims priority of the benefits of the filing of PCT Application No. PCT/EP2007/060539, filed Oct. 4, 2007, and European Patent Convention Patent Application No. 06121756.8 filed Oct. 4, 2006. The complete disclosures of the aforementioned related U.S. patent application is/are hereby incorporated herein by reference for all purposes.

FIELD OF THE INVENTION

The present invention relates to the use of carboxamide 4-[(4-pyridyl)amino]-pyrimidines as inhibitors of HCV replication as well as their use in pharmaceutical compositions aimed to treat or combat HCV infections. The present invention also concerns processes for the preparation of such compounds, pharmaceutical compositions comprising them, and combinations of said compounds with other anti-HCV agents.

BACKGROUND ART

Hepatitis C virus is the leading cause of chronic liver disease worldwide and has become a focus of considerable medical research. HCV is a member of the Flaviviridae family of viruses in the *hepacivirus* genus, and is closely related to the *flavivirus* genus, which includes a number of viruses implicated in human disease, such as dengue virus and yellow fever virus, and to the animal pestivirus family, which includes bovine viral diarrhea virus (BVDV).

There are 6 major HCV genotypes and more than 50 subtypes, which are differently distributed geographically. HCV type 1 is the predominant genotype in the US and Europe. For instance, HCV type 1 accounts for 70 to 75 percent of all HCV infections in the United States. The extensive genetic heterogeneity of HCV has important diagnostic and clinical implications, perhaps explaining difficulties in vaccine development and the lack of response to therapy. An estimated 170 million persons worldwide are infected with hepatitis C virus (HCV).

HCV replicates preferentially in hepatocytes but is not directly cytopathic, leading to persistent infection. In particular, the lack of a vigorous T-lymphocyte response and the high propensity of the virus to mutate appear to promote a high rate of chronic infection. As such, subsequent to an initial acute infection, a majority of infected individuals develop chronic hepatitis, which can progress to liver fibrosis leading to cirrhosis, end-stage liver disease, and HCC (hepatocellular carcinoma) (National Institutes of Health Consensus Development Conference Statement: Management of Hepatitis C. *Hepatology*, 36, 5 Suppl. S3-S20, 2002).

Transmission of HCV can occur through contact with contaminated blood or blood products, for example following blood transfusion or intravenous drug use. After initial exposure to the Hepatitis C virus, HCV RNA can be detected in blood in 1-3 weeks. Within an average of 50 days virtually all patients develop liver cell injury. The majority of patients are asymptomatic and anicteric. Only 25-35 percent develop malaise, weakness, or anorexia, and some become icteric. Antibodies to HCV (anti-HCV) almost invariably become detectable during the course of illness. Anti-HCV can be detected in 50-70 percent of patients at the onset of symptoms and in approximately 90 percent of patients 3 months after onset of infection. HCV infection is self-limited in only 15 percent of cases. Recovery is characterized by disappearance of HCV RNA from blood and return of liver enzymes to normal.

About 85 percent of HCV-infected individuals fail to clear the virus by 6 months and develop chronic hepatitis with persistent, although sometimes intermittent, viremia. This capacity to produce chronic hepatitis is one of the most striking features of HCV infection. Chronic hepatitis C is typically an insidious process, progressing, if at all, at a slow rate without symptoms or physical signs in the majority of patients during the first two decades after infection. Symptoms first appear in many patients with chronic hepatitis C at the time of development of advanced liver disease.

In chronic hepatitis, inflammatory cells infiltrate the portal tracts and may also collect in small clusters in the parenchyma. The latter instance is usually accompanied by focal liver cell necrosis. The margin of the parenchyma and portal tracts may become inflamed, with liver cell necrosis at this site (interface hepatitis). If and when the disease progresses, the inflammation and liver cell death may lead to fibrosis. Mild fibrosis is confined to the portal tracts and immediately adjacent parenchyma. More severe fibrosis leads to bridging between portal tracts and between portal tracts and hepatic veins. Such fibrosis can progress to cirrhosis, defined as a state of diffuse fibrosis in which fibrous septae separate clusters of liver cells into nodules. The extent of fibrosis determines the stage of disease and can be reliably assessed. Severe fibrosis and necroinflammatory changes predict progression to cirrhosis. Once cirrhosis is established, complications can ensue that are secondary to liver failure and/or to portal hypertension, such as jaundice, ascites, variceal hemorrhage, and encephalopathy. The development of any of these complications marks the transition from a compensated to a decompensated cirrhosis.

Chronic hepatitis C infection leads to cirrhosis in at least 20 percent of patients within 2 decades of the onset of infection. Cirrhosis and end-stage liver disease may occasionally develop rapidly, especially among patients with concomitant alcohol use. Chronic infection by HCV is associated with an increased risk of liver cancer. The prevailing concept is that hepatocellular carcinoma (HCC) occurs against a background of inflammation and regeneration associated with chronic hepatitis over the course of approximately 3 or more decades. Most cases of HCV-related HCC occur in the presence of cirrhosis.

Liver fibrosis is one of the processes that occurs when the liver is damaged. Such damage may be the result of viral activity as explained hereinabove (e.g., chronic hepatitis types B or C) or other liver infections (e.g., parasites, bacteria); chemicals (e.g., pharmaceuticals, recreational drugs, excessive alcohol, exposure to pollutants); immune processes (e.g., autoimmune hepatitis); metabolic disorders (e.g., lipid, glycogen, or metal storage disorders); or cancer growth (primary or secondary liver cancer). Fibrosis is both a sign of liver damage and a potential contributor to liver failure via progressive cirrhosis of the liver.

It has been disclosed that the inhibition of the family of TGFβ kinases is useful in the treatment of fibroproliferative disorders, including liver fibrosis. However, as it is noted above, liver fibrosis may be caused by different etiological agents, including the Hepatitis C virus. Most importantly, liver fibrosis is a specific condition in the disease progression of patients infected with HCV.

WO04/024159 discloses substituted pyrimidines and triazines which are useful in the treatment of conditions associated with enhanced TGFβ activity.

It has been surprisingly found that the compounds of the present invention inhibit HCV replication. HCV replication refers to the process of reproducing or making copies of HCV RNA. In the present invention HCV replication both refers to the replication of the HCV virus as a whole or the replication of the HCV RNA genome.

The compounds of the present invention are thus able to treat HCV infected patients at early stages in order to avoid disease progression, thereby avoiding that the patient develops chronic hepatitis, liver fibrosis, cirrhosis, hepatocellular carcinoma (HCC), or death.

In addition, the compounds of the invention are valuable in that they can diminish the HCV viral load of a patient, or can diminish the HCV viral load of a patient to undetected levels.

The compounds of the invention herein are derivatives of pyrimidine. PCT publication WO01/47921 describes pyrimidine and triazine compounds that are inhibitors of kinase activities associated with various inflammatory conditions, as opposed to the treatment of fibroproliferative disorders described herein. The above mentioned PCT publication describes the use of the compounds disclosed only for treatment of the inflammatory aspects of certain autoimmune diseases. Further, the compounds described differ from those described herein by virtue of the substitutions required on the pyrimidine nucleus; among other distinctions, the compounds disclosed in the PCT publication do not include phenyl bound directly to the pyrimidine ring.

Related compounds, some of which have the 4-pyridylamine group at C-4 on the pyrimidine, are disclosed in published U.S. Patent Applications, publications no. US 2004-0132730 A1, US 2004-0132159-A1 and US 2005/0004143-A1. Those applications, however, disclose a preference for certain electron-donating substituents on the pyridine ring of the 4-pyridylamine group, including alkyl, amine and alkoxy groups, without disclosing a preferred position for those substituents, or they suggest a variety of aryl groups which may be pyridyl for the 4-position substituent on a pyrimidine ring but do not disclose or suggest the combination of features of the present invention, in particular they do not suggest the amides of the present invention. The present invention provides compounds specifically including a 4-pyridylamine that is substituted by a carboxamide group which is attached at position 3 on the pyridine ring. The carboxamide is attached via its carbonyl carbon, and is typically a secondary amide; furthermore, the compounds of the present invention include specific functional groups and substituents particularly on the amide group, that are selected for their ability to reduce metabolism and increase bioavailability of the active species.

U.S. Pat. No. 6,476,031 ('031) also discloses compounds containing a quinazoline ring linked to an aryl group at C-4 of the quinazoline. The compounds are reported to act at the TGFβ site, and some of the compounds include a 4-pyridylamine group at C-4 of the quinazoline. However, the '031 patent discloses that the aryl group linked to C-4 of the quinazoline is preferably unsubstituted 4-pyridyl, and it does not disclose any compounds where the 4-pyridyl includes an amide substituent such as the ones at the 3-position of the 4-pyridyl group in the compounds of the present invention.

DISCLOSURE OF THE INVENTION

The present invention concerns the use of the compound of formula (I) in the manufacture of a medicament for the treatment of an infection with hepatitis C virus. The compounds of the invention can be represented by formula (I):

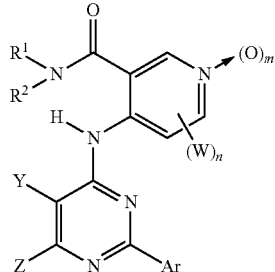

wherein Ar represents an optionally substituted phenyl ring;
Y represents H, halo, NO$_2$, or an optionally substituted member selected from the group consisting of alkyl, cycloalkyl, alkenyl, alkynyl, heteroalkyl, heteroalkenyl, heteroalkynyl, aryl, heteroaryl, arylalkyl, heteroarylalkyl, acyl, and heteroacyl,
  or Y can be NR$_2$, wherein each R is independently H or an optionally substituted alkyl, cycloalkyl, alkenyl, alkynyl, acyl, aryl or arylalkyl group or a heteroform of any of these groups, and wherein two R groups can cyclize to form an optionally substituted 3-8 membered heterocyclic ring;
R$^1$ represents an optionally substituted group selected from alkyl, cycloalkyl, heteroalkyl, acyl, alkoxy, alkylamino, heteroacyl, aryl, heteroaryl, arylalkyl, and heteroarylalkyl, where each heteroalkyl, heteroacyl, heteroaryl, and heteroarylalkyl includes one or more heteroatoms selected from O, N, S and P,
  provided that R$^1$ is not a group of the formula —CH$_2$—CH(OH)—R$^4$, where R$^4$ is H or an optionally substituted hydrocarbyl group that does not comprise an amine;
R$^2$ represents H, or R$^2$ represents CH$_2$ and R$^1$ and R$^2$ cyclize to form an optionally substituted piperidine, morpholine, or piperazine ring, or a pyrrolidine ring substituted with at least one amino or halo substituent;
Z represents H, halo, NO$_2$, or an optionally substituted member selected from the group consisting of alkyl, cycloalkyl, alkenyl, alkynyl, heteroalkyl, heteroalkenyl, heteroalkynyl, aryl, heteroaryl, arylalkyl, heteroarylalkyl, acyl, and heteroacyl, or Z is NR$_2$,
  wherein each R is independently H or an optionally substituted alkyl, cycloalkyl, alkenyl, alkynyl, acyl, heteroacyl, aryl or arylalkyl group or a heteroform of any of these groups;
each W independently represents halo, NR$_2$, NO$_2$, CN, CF$_3$, or an optionally substituted member selected from the group consisting of alkyl, cycloalkyl, alkenyl, alkynyl, heteroalkyl, heteroalkenyl, heteroalkynyl, aryl, heteroaryl, acyl, heteroacyl, arylalkyl, and heteroarylalkyl,
  wherein each R is independently H or an optionally substituted alkyl, cycloalkyl, alkenyl, alkynyl, acyl, aryl, heteroalkyl or heteroaryl group;
m is 0 or 1;
n is 0-3; and
  (a) Y is selected from the group consisting of a 5-6 membered cyclic amine, OH, F, Cl, Br, and I; or
  (b) m is 1; or
  (c) R$^1$ is OH or an optionally substituted alkoxy or an optionally substituted alkylamine, or (d) $R^2$ represents $CH_2$ and $R^1$ and $R^2$ cyclize to form an optionally substituted piperidine, morpholine, or piperazine ring, or a pyrrolidine ring substituted with at least one amino or halo substituent;

(e) $R^1$ comprises C—$NH_2$, a nitrile, a lactam or a lactone ring, or a ketone, or an optionally substituted 4-5 membered cyclic amine; or (f) $R^1$ comprises at least two substructures independently selected from the group consisting of:
  (1) C—NH—C,
  (2) C—OH,
  (3) C=O,
  (4) P=O,
  (5) S=O,
  (6) C=N,
  (7) a non-cyclic ether oxygen,
  (8) a tertiary non-acylated amine;
  (9) a 5-6 membered aromatic or heteroaromatic ring,
  (10) C—X where X is selected from OH, Cl, and F,
  (11) $C_T$—O—$R^4$, wherein $C_T$ represents a carbon bonded to three other carbon atoms, and $R^4$ is H or an optionally substituted hydrocarbyl group, and
  (12) an optionally substituted 3 to 8 membered carbocyclic ring; or (g) $R^1$ comprises —$(CH_2)_3$—$OR^4$ or —$(CH_2)_3$—$N(R^4)_2$, wherein each $R^4$ is independently H or an optionally substituted hydrocarbyl group;

or a pharmaceutically acceptable salt thereof.

The invention is also directed to pharmaceutical compositions containing one or more compounds of formula (I) or their pharmaceutically acceptable salts, including certain prodrug forms of such compounds, as active ingredients, and to methods of treating conditions characterized by an excessive level of TGFβ activity or fibroproliferative conditions or cancers using these compounds and compositions.

The invention also relates to the use of a compound of formula (I), or their pharmaceutically acceptable salts, including certain prodrug forms of such compounds, for the manufacture of a medicament for inhibiting HCV replication. The invention relates to a method of treating an infection with hepatitis C virus in a warm-blooded animal said method comprising the administration of an effective amount of a compound of formula (I), or their pharmaceutically acceptable salts, including certain prodrug forms of such compounds; and the invention further relates to a method of inhibiting HCV replication in a warm-blooded animal said method comprising the administration of an effective amount of a compound of formula (I), or their pharmaceutically acceptable salts, including certain prodrug forms of such compounds.

The compounds of formula (I) show activity against the HCV virus and are therefore useful as a medicament, and in the manufacture of a medicament for preventing, treating or combating an infection with hepatitis C virus other than liver fibrosis. Equally, the invention provides a method of preventing, treating or combating an infection with hepatitis C virus other than liver fibrosis.

MODES OF CARRYING OUT THE INVENTION

As used herein the term "hydrocarbyl" refers to a C1-C20 hydrocarbon group that may contain alkyl chains, rings, or combinations of chains and rings, and may contain one or more unsaturated and/or aromatic structures, but which contains no heteroatoms unless it is substituted. A hydrocarbyl group may be substituted at any available position with suitable substituents as further described herein.

As used herein, the terms "alkyl," "alkenyl" and "alkynyl" include straight-chain, branched-chain monovalent hydrocarbyl radicals, and combinations of these, which contain only C and H when they are unsubstituted. Examples include methyl, ethyl, isobutyl, 2-propenyl, 3-butynyl, and the like. The total number of carbon atoms in each such group is sometimes described herein, e.g., either as 1-10C or as C1-C10 when the group can contain up to ten carbon atoms. When heteroatoms (N, O and S typically) are allowed to replace carbon atoms as in heteroalkyl groups, for example, the numbers describing the group represent the sum of the number of carbon atoms in the group plus the number of such heteroatoms that are included as replacements for carbon atoms.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, C1-C8 alkyl, C2-C8 heteroalkyl, C1-C8 acyl, C2-C8 heteroacyl, C6-C10 aryl or C5-C10 heteroaryl.

"Heteroalkyl", "heteroalkenyl", and "heteroalkynyl" are defined similarly to the corresponding hydrocarbyl (alkyl, alkenyl and alkynyl) groups, but the 'hetero' terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form a heteroalkyl, heteroalkenyl, or heteroalkynyl group. The typical and preferred sizes for heteroforms of alkyl, alkenyl and alkynyl groups are the same as for the corresponding hydrocarbyl groups, and the substituents that may be present on the heteroforms are the same as those described above for the hydrocarbyl groups. For reasons of chemical stability, it is also understood that, unless otherwise specified, such groups do not include more than two contiguous heteroatoms except where an oxo group is present on N or S as in a nitro or sulfonyl group.

The term "cycloalkyl" is used herein to describe a carbocyclic non-aromatic group that is connected via a ring carbon atom, and "cycloalkylalkyl" may be used to describe a carbocyclic non-aromatic group that is connected to the molecule through an alkyl linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings. Typical heteroaromatic systems include monocyclic C5-C6 aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, enzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms. Preferably the monocyclic heteroaryls contain 5-6 ring members, and the bicyclic heteroaryls contain 8-10 ring members.

Aryl and heteroaryl moieties may be substituted with a variety of substituents including halo, C1-C8 alkyl, C2-C8 alkenyl, C2-C8 alkynyl, OR, NR$_2$, SR, SO$_2$R, SO$_2$NR$_2$, NRSO$_2$R, NRCONR$_2$, NRCOOR, NRCOR, CN, COOR, CONR$_2$, OOCR, COR, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R is optionally substituted as described above for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a C1-C4 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a C5-C6 monocyclic heteroaryl group that is optionally substituted with the groups described above as substituents typical on aryl groups and a C1-C4 alkylene that is unsubstituted or is substituted with one or two C1-C4 alkyl groups or heteroalkyl groups, or it includes an optionally substituted phenyl ring or C5-C6 monocyclic heteroaryl and a C1-C4 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_n$— where n is 1-8 and preferably n is 1-4, though where specified, an alkylene can also be substituted by other groups, and can be of other lengths, and the open valences need not be at opposite ends of a chain. Thus —CH(Me)- and —C(Me)$_2$- may also be referred to as alkylenes. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, $R^7$ is alkyl, this alkyl may optionally be substituted by the remaining substituents listed as embodiments for $R^7$ where this makes chemical sense, and where this does not undermine the size limit provided for the alkyl per se; e.g., alkyl substituted by alkyl or by alkenyl would simply extend the upper limit of carbon atoms for these embodiments, and is not included. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced accordingly.

"Halo", as used herein includes fluoro, chloro, bromo and iodo. Fluoro and chloro are often preferred.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

The Invention Compounds

The compounds useful in the invention are derivatives of pyrimidine containing mandatory substituents at positions corresponding to the 2- and 4-positions of the pyrimidine ring. The compounds include a 4-pyridylamine group at position 4 of the pyrimidine ring and a phenyl group at position 2 of the pyrimidine ring; each of these may be substituted. Optionally, the 4-pyridyl group may be a pyridine-N-oxide.

The compounds further include an amide group that is attached to the pyridyl ring at its position 3; this amide group is connected to the pyridyl ring through its carbonyl carbon. The nitrogen of the amide may have one hydrogen and one non-hydrogen substituent, $R^1$, attached to it, or it may be part of a ring formed by cyclizing $R^1$ onto a $CH_2$ group represented by $R^2$. Accordingly, the compounds all share a common skeleton, and differ in the nature of certain optional substituents on the aryl rings and on the nitrogen of the carboxamide shown in formula (I).

The substituent $R^1$ of this carboxamide may be selected to avoid certain metabolic pathways that have been found to reduce the activity of certain compounds previously reported. Similarly, the substituents on $R^1$ may be selected to promote water solubility and bioavailability.

For example, it has been found that if the amide in compounds related to the compound of formula (I) is of the form C(=O)—NH—$CH_2$—CH(OH)—R, the secondary hydroxyl in this amide group is readily oxidized in vivo. Accordingly, the present invention provides compounds less prone to such oxidation, such as compounds that incorporate an additional substituent on the portion of the amide containing this hydroxyl, in order to prevent or slow such oxidative metabolism. For example, by making the secondary alcohol into a tertiary alcohol, its oxidation is prevented. Alternatively, additional substituents may be placed around the hydroxyl-bearing carbon to slow the oxidative process, as in C(=O)—NH—CHR'—CH(OH)—R, where the added R' is positioned to sterically slow down that oxidation. In other examples, the secondary hydroxyl is modified into an ether or an ester or a phosphate ester; and they may also serve as prodrugs of the secondary alcohol. Such prodrugs can prolong delivery of the secondary alcohol by releasing the alcohol compound gradually in vivo as the prodrug undergoes metabolic cleavage to the free secondary alcohol, such as by ester or phosphate ester hydrolysis.

Similarly, the addition of hydrogen bond accepting groups in $R^1$, such as C=O, S=O, P=O, C=N, C≡N, certain ether oxygens, and tertiary amines that are not acylated so they retain some basicity, can be employed to increase bioavailability, possibly by increasing the tendency of this part of the molecule to partition into an aqueous phase. Likewise, certain hydrogen bond donor substructures such as —OH and NH also can increase the effectiveness of the compounds of the invention, and are often suitably incorporated into the $R^1$ group of the amide in compounds of formula (I). Moreover, the incorporation of two such substructures into $R^1$ can enhance the activity of the compounds. Accordingly, in certain embodiments, the compounds of formula (I) include at least two substructures in $R^1$ that are selected from C—NH—C, C—OH, C=O, P=O, S=O, =N, a non-cyclic ether oxygen, a tertiary non-acylated amine, a 5-6 membered aromatic or heteroaromatic ring, certain optionally substituted cyclic amines, C—X where X is selected from Cl, F and CN, and an oxygen bonded to a tertiary carbon, of the formula $C_T$—O—$R^4$, where $R^4$ is H or an optionally substituted hydrocarbyl group, and $C_T$ represents a carbon bonded to three other carbon atoms. Likewise the activity of the compounds can be improved by certain substituents on the pyrimidine ring at position 5 (represented by the Y group), including halo (F, Cl, Br or I), cyclic amines having 5-8 ring members which may be connected to the pyrimidine ring by the amine nitrogen or by a ring carbon, or —OH. In other embodiments, $R^1$ comprises a lactam or lactone ring, or a ketone carbonyl. Preferably, the amide group containing $R^1$ is not of the formula C(=O)—NH—$CH_2$—CH(OH)—$R^4$, where $R^4$ is H or an optionally substituted hydrocarbyl group that does not contain an amine, which substructure appears to facilitate oxidative metabolic degradation.

As described above, $R^1$ can be selected to improve bioavailability of the compounds of the invention, and in many embodiments it includes one or more polar functional groups such as those listed above. It may comprise an aromatic ring; however, in many embodiments where it represents an aryl or heteroaryl group, that group is a polar ring such as a phenyl substituted with an amide group, or a heteroaryl group such as a pyrrole or imidazole ring, or a cyclic amine. In other embodiments, $R^1$ incorporates one or more halo substituents on an alkyl group, such as for example a trifluoromethyl, which can improve water solubility and also deter metabolism.

In some embodiments, $R^1$ is hydroxyl or an alkoxy or heteroalkoxy, or a substituted amine group, with O or N directly bonded to the carboxamide nitrogen to form an acyl hydrazide or a hydroxamate derivative; an optionally substituted C1-C8 alkoxy or C1-C8 heteroalkoxy is sometimes preferred. In other embodiments, $R^1$ is an optionally substituted alkyl, cycloalkyl, heteroalkyl, acyl, heteroacyl, aryl, arylalkyl, heteroaryl, or heteroarylalkyl group. Typically, $R^1$ is C1-C8 alkoxy, substituted amino, C1-C8 alkyl, C2-C8 heteroalkyl, C6-C10 aryl, C5-C10 heteroaryl, C7-C12-arylalkyl, or C6-C12 heteroarylalkyl, where each of the foregoing groups is optionally substituted by the substituents described herein as suitable for such groups. In many embodiments, $R^1$ is an optionally substituted C1-C8 alkyl or C1-C8 heteroalkyl group, which can be or include a cyclic group, that contains at least one and preferably two groups selected from those mentioned above, i.e., C—NH—C, C—OH, C=O, P=O, S=O, =N, a non-cyclic ether oxygen, a tertiary non-acylated amine, a 5-6 membered aromatic or heteroaromatic ring, CX where X is selected from Cl, F and CN, and an oxygen bonded to a tertiary carbon, of the formula $C_T$—O—$R^4$, where $R^4$ is H or an optionally substituted hydrocarbyl group, and $C_T$ represents a carbon bonded to three other carbon atoms. In some embodiments, $R^1$ includes a heterocyclic group having 3-8 ring members, at least one of which is a heteroatom selected from N, O and S; furanose and pyranose rings are sometimes included, and at other times a lactam, lactone, or 5-6 membered nonaromatic ring containing a nitrogen atom is included.

Preferred substituents for the groups comprising $R^1$ include hydroxyl, halo especially F or Cl, C1-C8 alkoxy, C1-C8 alkyl, C2-C8 heteroalkyl, CN, mono- and di-(C1-C8)-alkyl amines, —C(=O)R, COOR, $CONR_2$, —NC(O)R, —C(O)$NR_2$, —NRC(O)OR, $SO_2R$, $SO_2NR_2$, —OP(=O)(OR)$_2$, and, where available valences permit, =O, =N—OH, =N—(C1-C8 alkyl), and =N—(C2-C8-heteroalkyl). Each R in these substituents is independently H, C1-C8 alkyl, C2-C8 heteroalkyl, C6-C10 aryl, C5-C10 heteroaryl, C1-C8 acyl or C2-C8 heteroacyl. Preferred embodiments of $R^1$ include H, OR, NHR, C1-C8 alkyl and C2-C8 heteroalkyl, wherein each R represents H or C1-C8 alkyl or C2-C8 heteroalkyl, and each alkyl or heteroalkyl is optionally substituted as just described.

In certain embodiments, $R^1$ is of the form $R_2$—C(OH)—$CH_2$— or R—CH(OH)—CHR— or HO—$CH_2$—CHR—, where each R is independently a C1-C8 alkyl or heteroalkyl group and may be substituted, and where two R groups can cyclize together to form a 3-8 membered ring that can include up to two heteroatoms selected form N, O and S as ring members. These embodiments are distinguished from compounds having $R^1$=R—CH(OH)—$CH_2$— because the additional R groups are positioned to slow oxidative metabolism that has been shown to occur with the latter group; thus these embodiments of $R^1$ promote the desired biological activity of the compound of formula (I).

In some embodiments, $R^1$ comprises a substituted alkyl, cycloalkyl or heteroalkyl group that is preferably cyclic and is linked to the amide nitrogen through an aminoalkylene group such as —NR—$(CH_2)_{2-4}$[N], where [N] represents the nitrogen of the carboxamide shown in formula (I). R in this linkage can be H or C1-C4 alkyl or heteroalkyl, which can be substituted with, for example, =O. In such embodiments, $R^1$ can include in addition to the linkage —NR—$(CH_2)_{2-4}$[N], a pyranose or furanose ring, which may be substituted and is in some instances substituted by one or more hydroxyl groups, preferably 2-4 hydroxyl groups, and which is either bonded directly to N of the linkage, or connected to that nitrogen by an optionally substituted C1-C4 alkylene or heteroalkylene linker such as $(CH_2)_{2-3}$ or —O$(CH_2)_{1-3}$, each of which can be substituted. In some such embodiments, this alkylene or heteroalkylene linker is substituted with one or two substituents such as, but not limited to, hydroxyl, =O, or C1-C4 alkyl. In other such embodiments, $R^1$ can comprise an aryl, heteroaryl, carbocyclic, or heterocyclic ring $R_n$ having 3-8 ring members, up to two of which can be heteroatoms selected from N, O and S, that is linked to the carboxamide of formula (I) through the above described aminoalkylene linker, e.g., $R_n$—$(CH_2)_{0-2}$—NR—$(CH_2)_{2-4}$[N]. In such embodiments, the ring $R_n$ or the linker connecting $R_n$ to the carboxamide nitrogen can include one or more ether linkages or be substituted with one or more substituents such as halo, hydroxyl, or C1-C4 alkoxy or an amino, C1-C4 alkylamino, or di-(C1-C4 alkyl)amino group.

In other embodiments where $R^1$ comprises a linking aminoalkylene group such as —NR—$(CH_2)_{2-4}$[N] as described above bonded to the carboxamide nitrogen, $R^1$ further comprises an acyl group such as RC(=O)—, RO—C(=O)—, or $R_2$N—C(=O)—, where each R independently represents H or an optionally substituted C1-C4 alkyl or heteroalkyl group. In such embodiments, $R^1$ can take the form R-Q-C(=O)—NR—$(CH_2)_{2-4}$[N], for example, where Q represents a bond, O or NR, and each R independently represents H or an optionally substituted C1-C4 alkyl or heteroalkyl group. Similarly, $R^1$ can comprise a sulfonyl, guanidinyl, or cyanoguanidinyl group attached through —NR—$(CH_2)_{2-4}$[N] as described above for the acyl groups.

In other embodiments where $R^1$ is linked to the carboxamide nitrogen through an aminoalkylene group such as —NR—$(CH_2)_{2-4}$[N] as described above, $R^1$ comprises a halogenated C1-C8 alkyl or heteroalkyl such as a polyfluorinated C1-C4 alkyl group, which can promote water solubility and slow metabolism. Specific examples of such embodiments include compounds having a group such as $CF_3CF_2$ $(CH_2)_{0-3}$—NR—$(CH_2)_{2-4}$[N] as $R^1$.

In other embodiments, $R^1$ comprises a lactam, lactone, or heterocyclic ring such as a 5-6 membered cyclic ether or acyclic amine having 4-5 ring members, each of which is optionally substituted with one or more substituents that can promote bioavailability, such as C1-C4 alkoxy, =O, halo such as one or more fluoro substituents, or CN, or with two or more hydroxyl substituents. In certain embodiments, $R^1$ is a dicarbonyl group such as RO—C(=O)—C(=O)— or $R_2$N—C(=O)—C(=O)—, where each R is independently H or C1-C8 optionally substituted alkyl or heteroalkyl group, or an optionally substituted C5-C12 aryl, arylalkyl, heteroaryl, or heteroarylalkyl group.

In certain embodiments, $R^1$ comprises $(CH_2)_3$—$OR^4$ or $(CH_2)_3$—N$(R^4)_2$. In these embodiments, each $R^4$ can be H or an optionally substituted C1-C20 hydrocarbyl group. Preferably, each $R^4$ is H or a C1-C4 alkyl, or N$(R^4)_2$ represents a 4-7 membered cyclic amine having up to two substituents suitable for an alkyl group and optionally including one additional heteroatom selected from N, O and S.

Other substituents may also be included on the pyrimidine, pyridine and aryl rings; in particular, the phenyl ring represented by Ar is optionally substituted with the groups described herein as suitable for placement on an aryl or heteroaryl ring, and may be substituted with 1-2 substituents selected from C1-C4 alkyl, C1-C4 alkoxy, $CF_3$, halo, and CN in certain embodiments.

The pyridyl ring (which may be referred to as a nicotinamide, due to the presence of the 3-position amide group) can be substituted with up to three substituents suitable for placement on an aryl ring, so n can be 0-3. Preferably, n is 0 or 1 in formula (I). In certain embodiments the pyridyl ring of formula (I) is substituted with one group selected from C1-C4 alkyl, C1-C4 alkoxy, $CF_3$, halo, and CN, and preferably selected from halo, methyl, $CF_3$, and OMe. In other embodiments, the pyridyl ring is not substituted other than by the amide shown in formula (I), i.e., n is 0.

Typical embodiments of W include the substituents described herein as substituents for an aryl group generally. These include including halo, R, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each R is optionally substituted with the same groups that may be present as substituents on the aryl group. Preferred embodiments for W include halo and CN, as well as $CF_3$, R, OR, SR, and $NR_2$, wherein each R is independently H or C1-C6 alkyl optionally substituted with =O or any of the substituents that can comprise W.

The pyrimidine ring may also be substituted with groups Y and Z at positions 5 and 6; these substituents are selected from those described herein as suitable for attachment to an aryl ring, and at least one such group is typically present, particularly at position 5.

Substituents represented by Y and Z, include, but are not limited to, alkyl, cycloalkyl, alkenyl, alkynyl, acyl, aryl, heteroalkyl, heteroalkenyl, heteroalkynyl, heteroacyl, arylalkyl, and heteroarylalkyl, each of which is optionally substituted by halo, =O (where two available valences are on a single atom), R, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, C5-C10 heteroaryl, C7-C12 arylalkyl, or C6-C12 heteroarylalkyl, and each R other than H is optionally substituted with the same groups that may be present as substituents on an aryl group. Additionally, Y and Z may independently be H, halo, OR, $NR_2$, SR, —SOR, —$SO_2R$, —OCOR, —NRCOR, —$NRCONR_2$, —NRCOOR, —$OCONR_2$, —COOR, $SO_2R$, NRSOR, $NRSO_2R$, —$SO_3R$, —$CONR_2$, $SO_2NR_2$, —CN, —$CF_3$, or $NO_2$, wherein each R is independently H, (1-8C) alkyl, (1-8C) heteroalkyl, (1-8C) acyl, (1-8C) heteroacyl, C6-C10 aryl, or C5-C10 heteroaryl and each R is optionally substituted with the same groups described above as suitable substituents for each group that comprises R.

Preferably, Y is not H, so position 5 of the pyrimidine ring is generally substituted. In certain embodiments, Y is selected from halo, OH, OR, $NR_2$, and R, wherein each R is an optionally substituted group selected from C1-C8 alkyl, C1-C8 heteroalkyl, C6-C12 arylalkyl, and C6-C12 heteroarylalkyl, and where two R groups of $NR_2$ can optionally cyclize to form 3-8 membered ring containing 1-2 heteroatoms selected from N, O and S. Preferred embodiments of Y include methoxy, ethoxy, propoxy, and isopropoxy; dimethylamino, pyrrolidin-1-yl, piperidine-1-yl, and morpholin-4-yl; and methyl, ethyl, propyl, isopropyl, cyclopropyl, t-butyl, cyclobutyl, and cyclopentyl.

Position 6 of the pyrimidine can also be substituted, so that Z can represent a substituent such as halo, $NO_2$, or an optionally substituted member selected from the group consisting of alkyl, cycloalkyl, alkenyl, alkynyl, heteroalkyl, heteroalkenyl, heteroalkynyl, aryl, heteroaryl, arylalkyl, heteroarylalkyl, acyl, and heteroacyl, or Z is $NR_2$, wherein each R is independently H or an optionally substituted alkyl, cycloalkyl, alkenyl, alkynyl, acyl, heteroacyl, aryl or arylalkyl group or a heteroform of any of these groups. While position 6 of the pyrimidine can be so substituted, in many embodiments it is unsubstituted, i.e., Z represents H.

Ar represents an optionally substituted phenyl; in many embodiments, Ar represents phenyl that is substituted with at least one and preferably two or more substituents selected from the group consisting of halo, CN, $CF_3$, R, OR, $NO_2$, SR, $SO_2R$, $NR_2$, and acyl, where each R is independently H, C1-C6 alkyl, C1-C8 acyl, or aryl. In many embodiments, Ar is substituted with at least one halo, and in certain embodiments it is substituted with 1-2 groups selected from C1-C4 alkyl, C1-C4-alkoxy, $CF_3$, CN and halo; halo in such embodiments is sometimes preferably Cl or F. Certain embodiments of Ar include phenyl substituted with F or Cl ortho to the carbon through which the phenyl is linked to the pyrimidine ring, which is referred to as position 2 for convenient reference. In some such embodiments, Ar further comprises a second substituent which may also be halo at position 5. A preferred embodiment for Ar, which may be combined with the preferred features of each of the other structural components of the compound of formula (I), has F or Cl at position 2 and Cl or F at position 5 of the phenyl ring.

A subgroup of compounds of the invention are those compounds of formula (I) or any of the subgroups of compounds of formula (I) wherein the compounds have the formula (II):

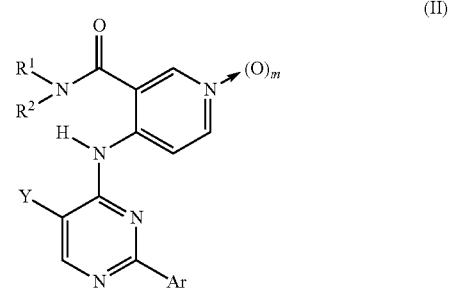

and the salts, and stereoisomers thereof, wherein
$R^1$, $R^2$, Y, and m are as defined for the compounds of formula (I) or any subgroup thereof;
Ar is a phenyl optionally substituted with one or two halo.

Another subgroup of compounds of the invention are those compounds of formula (I) or any of the subgroups of compounds of formula (I) wherein the compounds have the formula (III):

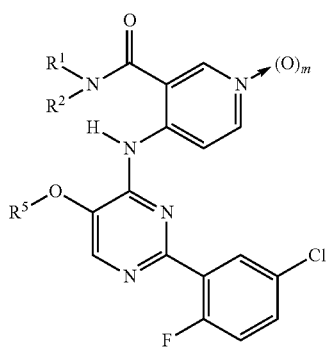

(III)

and the salts, and stereoisomers thereof, wherein
$R^1$, $R^2$, and m are as defined for the compounds of formula (I) or any subgroup thereof, and
$R^5$ is alkyl substituted with two halo; or $R^5$ is alkoxyalkyl.

As stated above, any aryl, alkyl, cycloalkyl, heteroaryl, heteroalkyl, acyl, heteroacyl, arylalkyl, or heteroarylalkyl group included within a substituent may itself be substituted with the substituents typical for such groups. These substituents may occupy all available positions of the group, preferably 1-2 positions, or more preferably only one position.

Where any of the aryl moieties, including those depicted in formula (I) especially the phenyl moieties, is described as optionally containing at least two substituents, if those substituents can occupy adjacent positions on the aryl ring, they may, when taken together, form a 5-7 membered carbocyclic or heterocyclic ring. Examples of such rings include dioxolane fused onto a phenyl ring, or oxazole fused to a pyridine ring.

The compounds of formula (I) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, citric, alkylsulfonic, arylsulfonic, and glucuronic acids and the like. If a carboxyl moiety is present on the compound of formula (I), the compound may also be supplied as a salt with a pharmaceutically acceptable cation, such as sodium, potassium, or an ammonium salt.

In the event that any of the substituents of formula (I) contain chiral centers or rotational isomers (atropisomers), as some, indeed, do, the compounds of formula (I) include each stereoisomeric form thereof, both as an isolated stereoisomer and as a component of a mixture of these stereoisomeric forms. Such mixtures of stereoisomers may be racemic or may be enriched in one enantiomer of a pair of enantiomers where a single chiral center is present. Where more than one stereoisomeric center is present, the invention includes mixtures wherein either, neither or both centers are enriched in one stereoisomeric form.

Synthesis of the Invention Compounds

A number of synthetic routes may be employed to produce the compounds of the invention. In general, they may be synthesized from conventional starting materials using reactions known in the art. Illustrative methods are provided below, and additional methods are described in published patent applications US 2004-0132159-A1 and US 2005/0004143-A1, which are incorporated by reference for their description of these synthetic methods.

Scheme 1 shows a general method for constructing pyrimidine rings having the substitution pattern required for compounds of the invention. First, an amidine is prepared; these can typically be made from the corresponding aryl nitriles as illustrated. The amidine is then allowed to react with a substituted malonaldehyde derivative to provide a 2-aryl substituted pyrimidinone. The group represented by X in Scheme 1 is typically alkyl, aryl, cycloalkyl, alkoxy, or dialkylamino.

Scheme 1. General method prepare pyrimidinone intermediates.

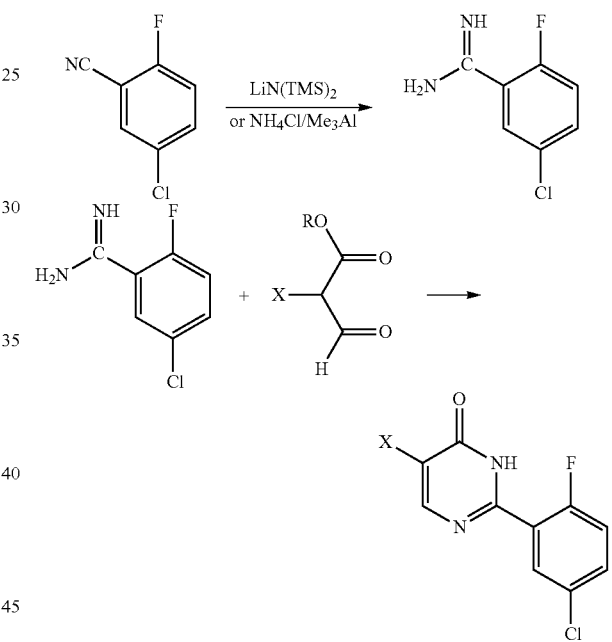

Scheme 2 illustrates a general strategy that was used to prepare many of the compounds of the invention, some of which are included in Table 1. The pyrimidinone ring is produced by cyclizing an amidine moiety as shown above, and the pyrimidinone is converted into a 4-halopyrimidine, typically with thionyl chloride/DMF or with POCl$_3$. The halo group on the pyrimidine ring is then displaced by a 3-substituted 4-aminopyridine to obtain a versatile intermediate having a carboxylate ester on the pyridine ring. This ester group is readily hydrolyzed to the free carboxylic acid as shown in Scheme 1, and then can easily be converted into a wide variety of carboxamides of the invention having the A group of formula (I) linked to the pyridyl ring through the carbonyl carbon.

The malonaldehydes required for this reaction are typically prepared by formylation of the corresponding esters, using LDA and ethyl formate. Using these conditions, compounds can readily be prepared wherein X represents an alkoxy, alkyl, aryl, heteroaryl, or dialkylamine, for example.

Scheme 2. General approach to synthesize numerous carboxamide compounds.

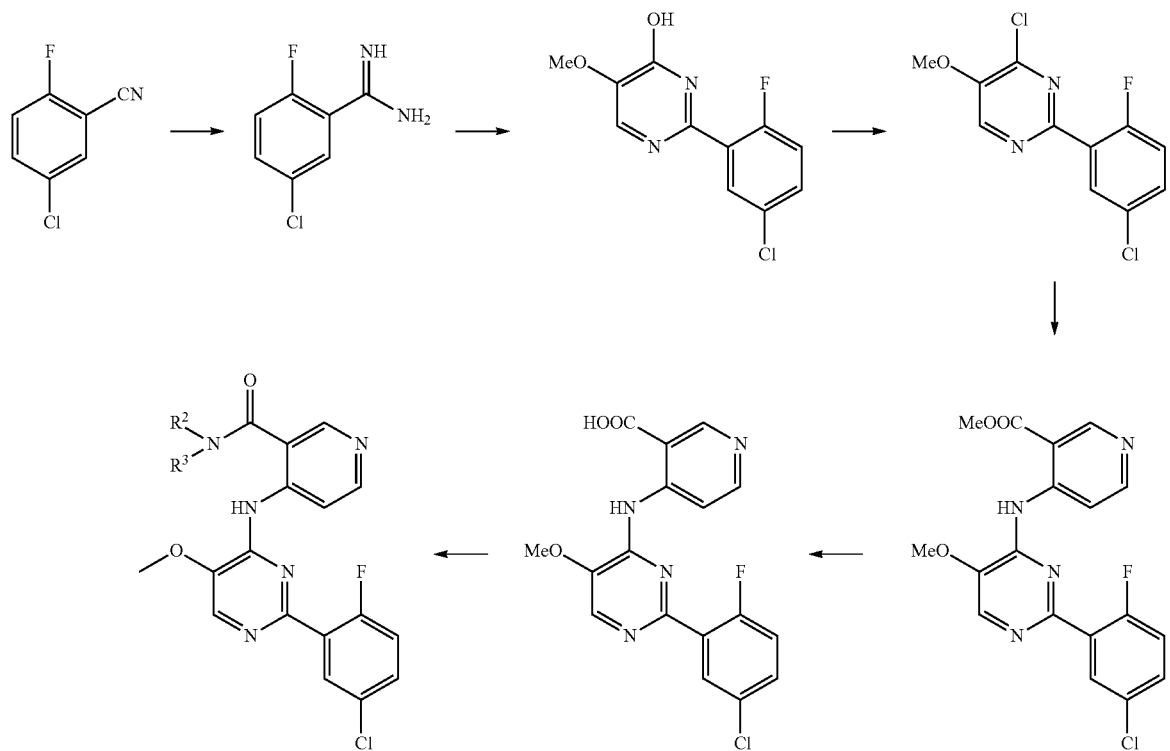

Reaction Schemes 3 and 4, shown below, provide routes to the pyrimidine nucleus that permit further substitution thereof. A malonate or cyanoacetate derivative is used to form the pyrimidinones in Schemes 3 and 4 rather than the malonaldehyde derivative used above. This provides pyrimidines having a substituent at position 6, corresponding to Z in formula (I).

Scheme 3

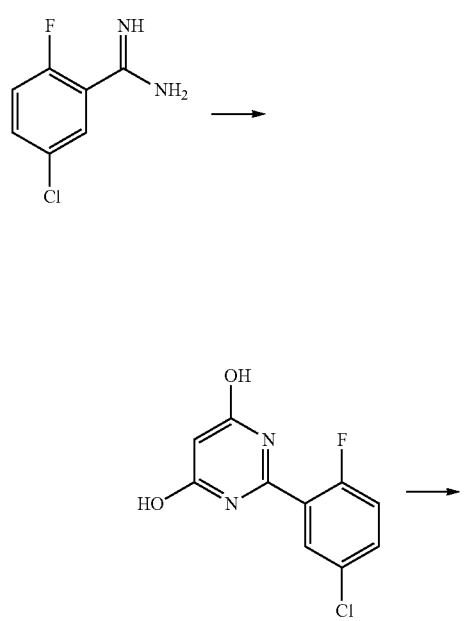

-continued

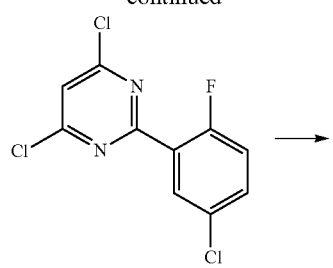

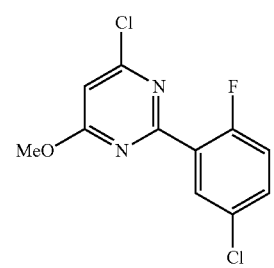

Scheme 4

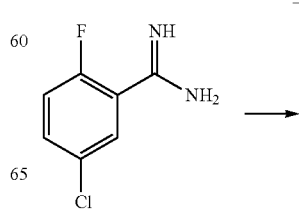

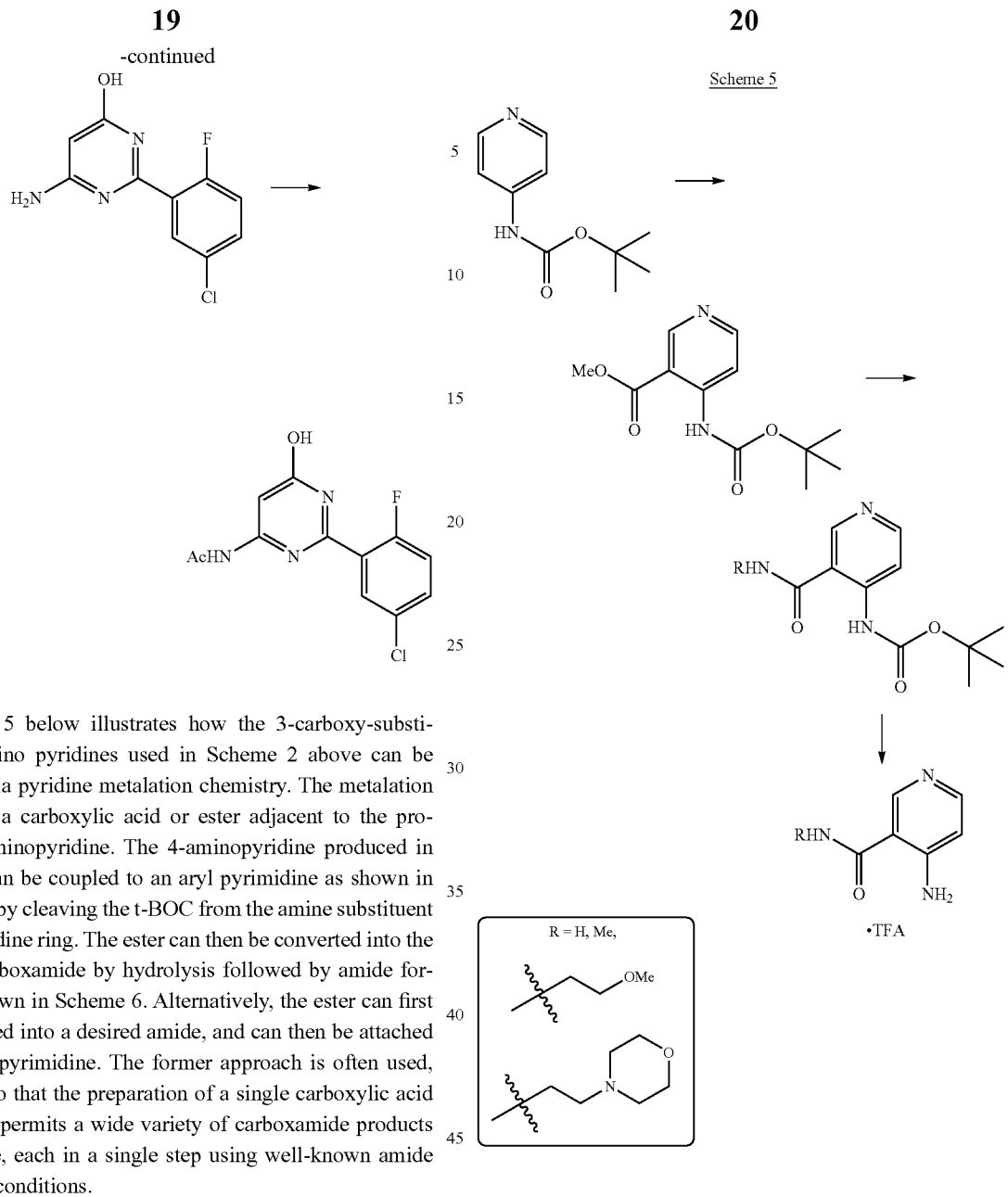

Scheme 5 below illustrates how the 3-carboxy-substituted-4-amino pyridines used in Scheme 2 above can be prepared via pyridine metalation chemistry. The metalation introduces a carboxylic acid or ester adjacent to the protected 4-aminopyridine. The 4-aminopyridine produced in this way can be coupled to an aryl pyrimidine as shown in Scheme 6, by cleaving the t-BOC from the amine substituent on the pyridine ring. The ester can then be converted into the desired carboxamide by hydrolysis followed by amide formation shown in Scheme 6. Alternatively, the ester can first be converted into a desired amide, and can then be attached to the halopyrimidine. The former approach is often used, however, so that the preparation of a single carboxylic acid compound permits a wide variety of carboxamide products to be made, each in a single step using well-known amide formation conditions.

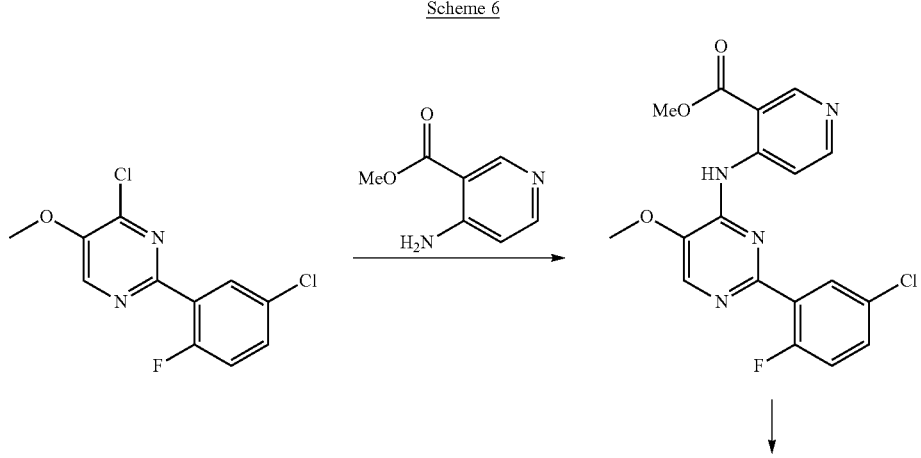

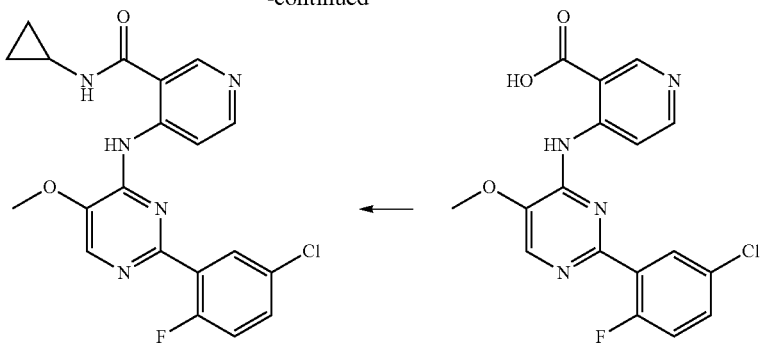

This scheme can be generally used to make 5-methoxy-pyrimidine compounds of the invention, and was employed to synthesize many of the compounds in Table 1. Furthermore, other 5-alkoxy derivatives are available from this scheme, because the methoxy group can be cleaved using lithium iodide in hot DMF as is known in the art. The resulting hydroxypyrimidine can be O-alkylated or otherwise derivatized under conditions well known for the introduction of alkoxy, acyloxy, and similar substituents.

Scheme 7

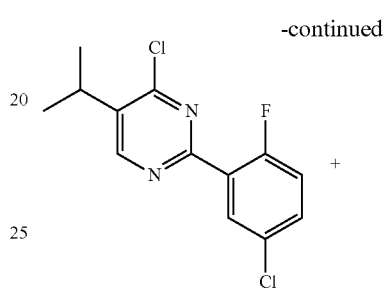

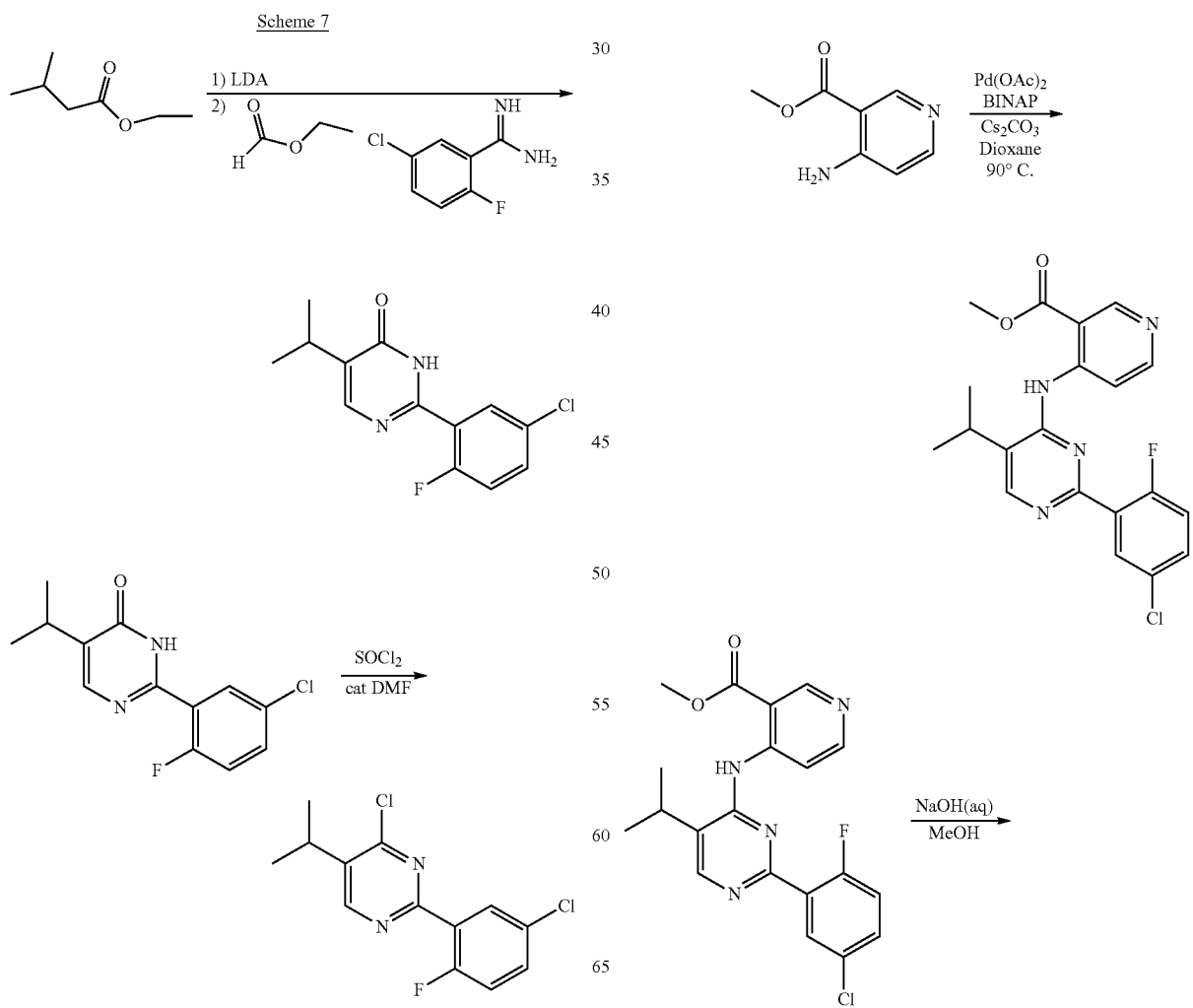

-continued

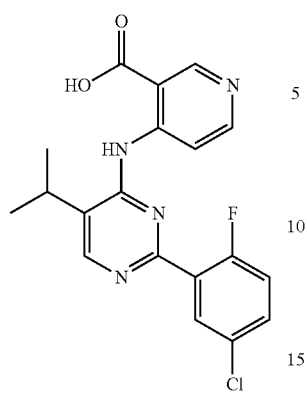

This scheme can be generally used to make isopropyl pyrimidines within the scope of the invention by coupling the carboxylic acid prepared in Scheme 7 with various amines. The use of a palladium catalyst to effect the coupling of the aminopyridine to the chloropyrimidine can be avoided by the use of a stronger base such as sodium hexamethyldisilazane as described in the Examples below (see Example 3).

-continued

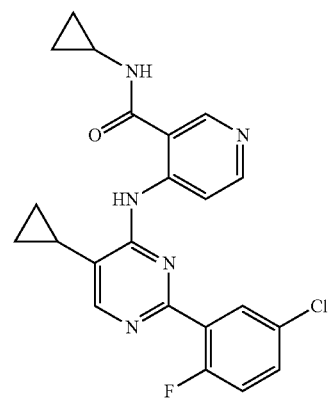

Scheme 8 depicts the preparation of a compound having a cyclopropyl group at position 5 of the pyrimidine ring. This method can be used to make 5-cyclopropyl pyrimidines having various carboxamide groups on the pyridine ring.

Scheme 9 depicts the corresponding synthesis of 5-cyclobutyl pyrimidine compounds, and shows the preparation of the methyl ester of cyclobutyl acetic acid from which the pyrimidine is constructed.

Scheme 8

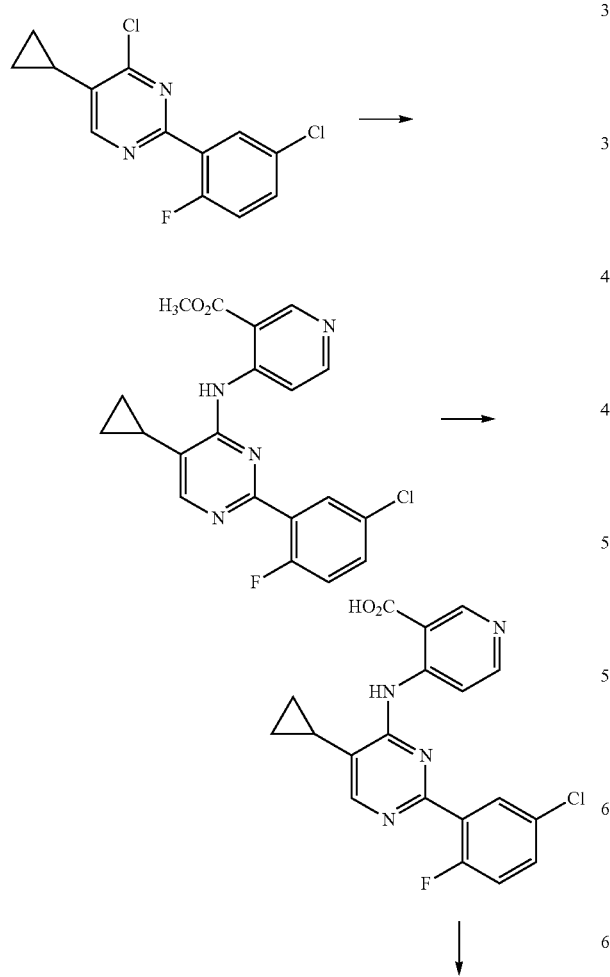

Scheme 9

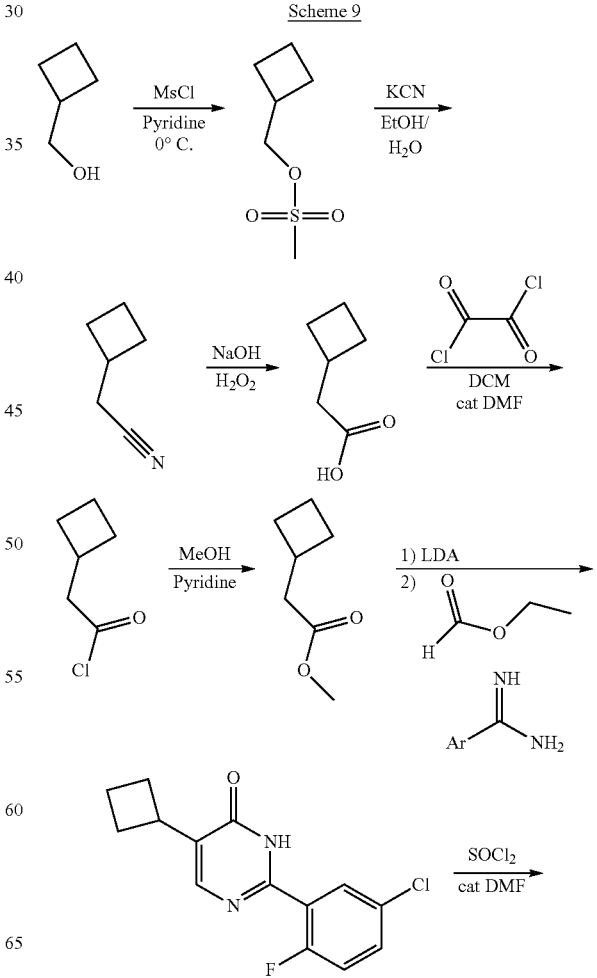

25

-continued

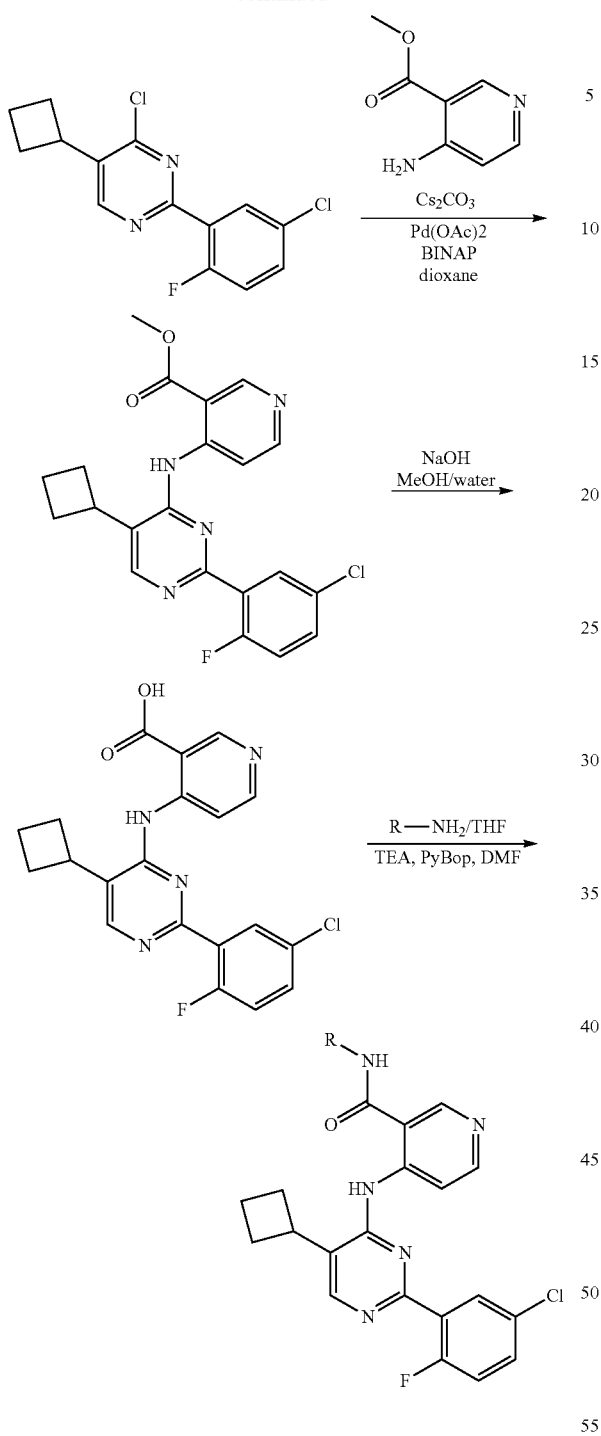

Scheme 10 shows the synthesis of 5-dimethylamino compounds of the invention using the same general approach. Cyclic amines can be introduced similarly.

Scheme 10

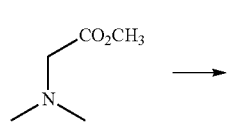

26

-continued

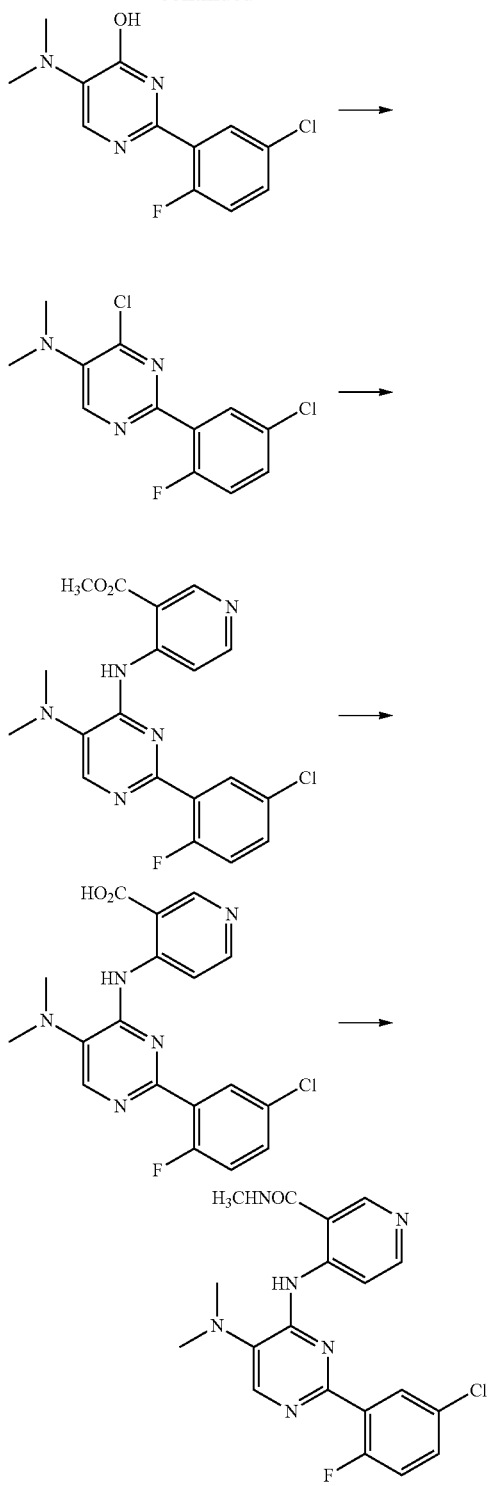

Scheme 11 can be generally used to make benzyloxy pyrimidines, including ones with substitution on the benzyl group, as well as to make other alkoxy substituted compounds. Like the methoxy compounds, these benzyloxy compounds can be used to make other 5-O substituted compounds by removing the benzyl group using a catalytic hydrogenation, for example, followed by alkylation or acylation of the resultant hydroxypyrimidine.

Scheme 11
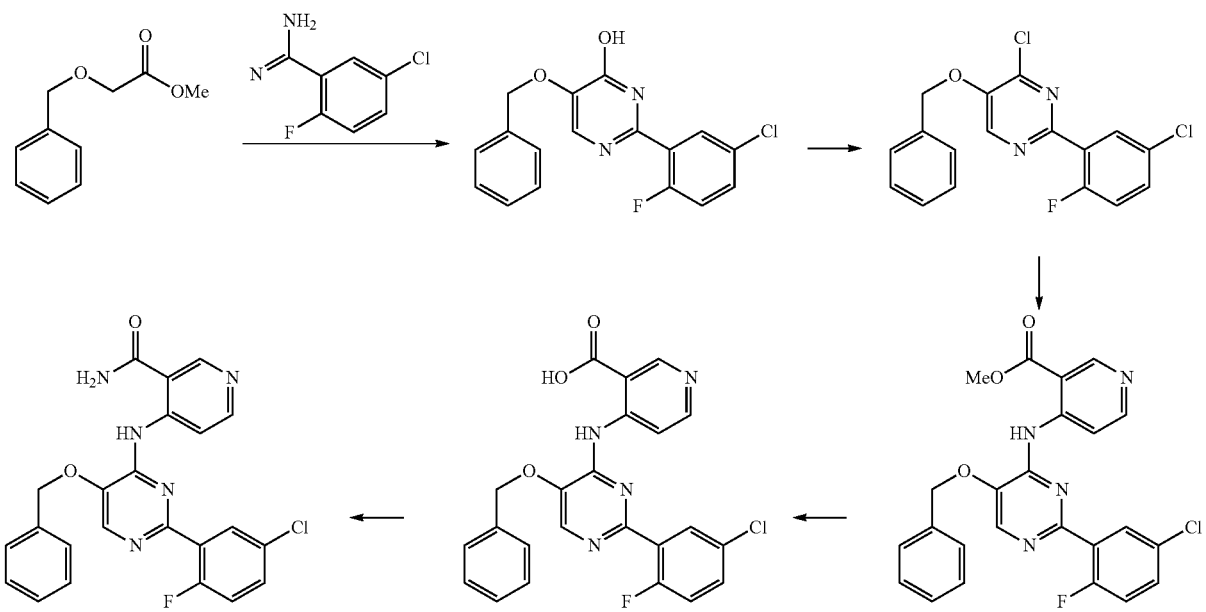
Scheme 12 illustrates use of the methods described above for the preparation of compound of the invention where Y in formula (I) is a tert-butyl group.
Scheme 12
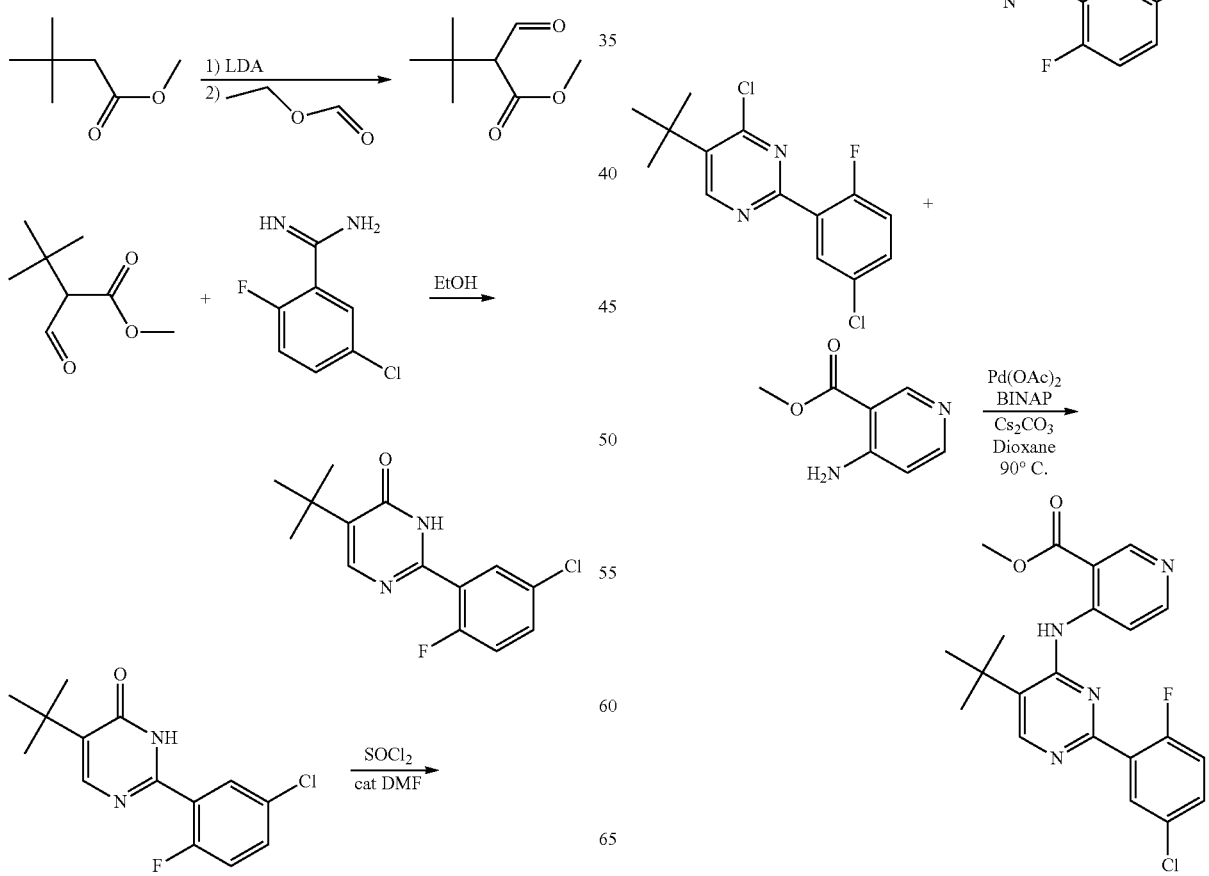
-continued
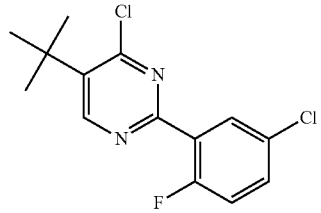

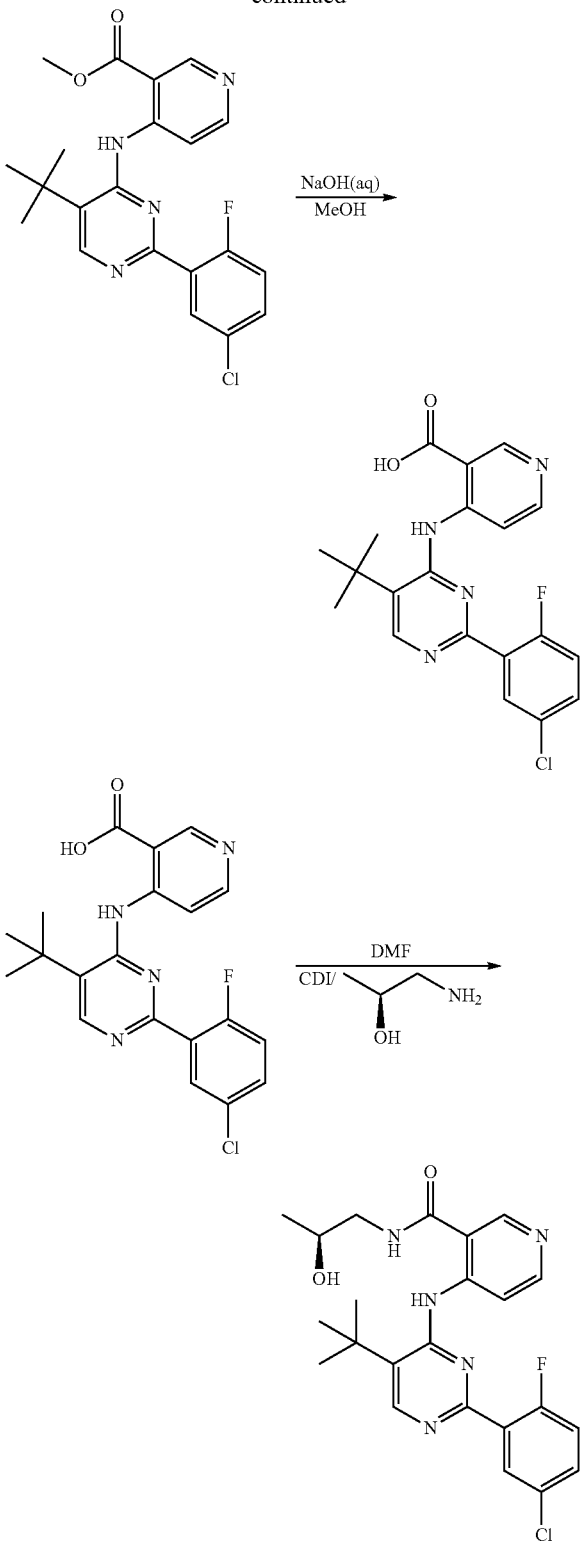

While this example shows the preparation of a compound where the group corresponding to $R^1$ in formula (I) has an undesired secondary hydroxyl, it can be used to introduce $R^1$ groups with a tertiary hydroxyl such as those described above, as well as many other variations of $R^1$ that are within the scope of formula (I) as described herein.

Where the pyridine N-oxides of compounds of formula (I) are desired, the pyridine compounds can be oxidized to N-oxides using commonly known oxidation reagents such as, for example, meta-chloroperoxy benzoic acid or peracetic acid.

Administration and Use

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. Said pharmaceutical composition is useful in the treatment of an infection with hepatitis C virus, and is also useful for inhibiting HCV replication The term "therapeutically effective amount" as used herein means that amount of active compound or component or pharmaceutical agent that elicits the biological or medicinal response in a tissue, system, animal or human that is being sought, in the light of the present invention, by a researcher, veterinarian, medical doctor or other clinician, which includes alleviation of the symptoms, prophylactic activity, stabilization and/or reduction of the disease being treated.

In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally an addition salt form thereof, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. The compounds of the present invention may be administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

In general it is contemplated that an antiviral effective daily amount of a compound of formula (I) would be from 0.001 mg/kg to 500 mg/kg body weight, more preferably from 0.01 mg/kg to 50 mg/kg body weight, and even more preferably from 0.01 mg/kg to 10 mg/kg body weight. It may be appropriate to administer the required dose as one, two, three, four or more (sub-)doses at appropriate intervals throughout the day. Said (sub-)doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorrhagic fever and encephalitis. A number of the compounds of this invention moreover can be active against mutated strains of HCV.

Due to their antiviral properties, particularly their anti-HCV properties, the compounds of formula (I) or any subgroup thereof, their N-oxides, addition salts, or stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

Also, the combination of previously known anti-HCV compound, such as, for instance, interferon-α (IFN-α), pegylated interferon-α and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV.

Anti-HCV compounds encompass agents selected from HCV polymerase inhibitors, NM283, R803, JTK-109 and JTK-003; HCV proteases (NS2-NS3 and NS3-NS4A) inhibitors, the compounds of WO02/18369 (see, e.g., page 273, lines 9-22 and page 274, line 4 to page 276, line 11), BILN-2061, VX-950, SCH 503034; inhibitors of other targets in the HCV life cycle, including helicase, and metalloprotease inhibitors, ISIS-14803; immunomodulatory agents such as, α-, β-, and γ-interferons, pegylated derivatized interferon-α compounds, compounds that stimulate the synthesis of interferon in cells, interleukins, compounds that enhance the development of type 1 helper T cell response, and thymosin; other antiviral agents such as ribavirin, amantadine, and telbivudine, inhibitors of internal ribosome entry, broad-spectrum viral inhibitors, such as IMPDH inhibitors (e.g., compounds of U.S. Pat. No. 5,807,876, U.S. Pat. No. 6,498,178, U.S. Pat. No. 6,344,465, U.S. Pat. No. 6,054,472, WO97/40028, WO98/40381, WO00/56331, and mycophenolic acid and derivatives thereof, and including, but not limited to VX-950, VX-497, VX-148, and/or VX-944); or combinations of any of the above.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and another HCV inhibitory compound, e.g. (pegylated) IFN-α and/or ribavirin.

In one embodiment of the present invention there is provided an article of manufacture comprising a composition effective to treat an infection with hepatitis C virus; and packaging material comprising a label which indicates that the composition can be used to treat an infection with hepatitis C virus; wherein the composition comprises a compound of the formula (I) or any subgroup thereof, or the combination as described herein.

Another embodiment of the present invention concerns a kit or container comprising a compound of the formula (I) or any subgroup thereof, or a combination according to the invention combining a compound of formula (I) or a pharmaceutically acceptable salt thereof, and an anti-HCV compound or a pharmaceutically acceptable salt thereof, in an amount effective for use as a standard or reagent in a test or assay for determining the ability of potential pharmaceuticals to inhibit HCV infection, growth, or both. This aspect of the invention may find its use in pharmaceutical research programs. As such, the compounds of the present invention can also be used in high-throughput target-analyte assays such as those for measuring the efficacy of said compounds in HCV treatment.

EXAMPLES

The following examples are intended to illustrate, but not to limit, the invention. Certain of the examples illustrate methods that are readily adapted to synthesis of compounds of formula (I), even though the specific example may not fit within formula (I) as described herein. As one of ordinary skill will appreciate, it is possible to combine various embodiments and synthesis methods described herein and to modify the starting materials by using well known or commercial alternatives to produce many variants that are not illustrated here: such combinations and variations are within the scope of the invention.

Example 1

Synthesis of [2-(3-chlorophenyl)-pyrimidin-4-yl]pyridin-4-yl amine

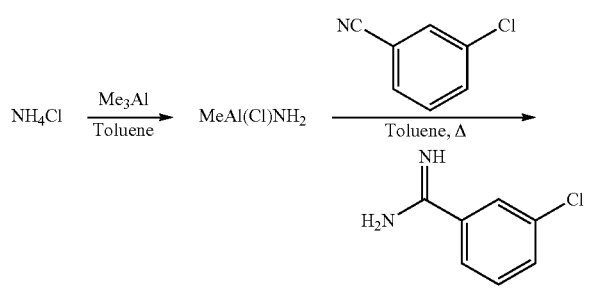

To a vigorously stirred, cooled (0° C.) suspension of (pestle-ground) ammonium chloride (1.17 g, 21.8 mmol) in dry toluene (7 mL) was added a solution of trimethylaluminum (10.9 mL, 2M solution in hexanes, 21.8 mmol) dropwise over 20 min. Effervescence occurred on addition. The mixture was stirred at r.t. for 15 min. To this solution was added a solution of 3-chlorobenzonitrile (1.0 g, 7.2 mmol) in dry toluene (5 mL) dropwise over 10 min. The solution was heated to 80° C. for 12 h then cooled and transferred slowly into a vigorously stirred slurry of silica gel (30 g) in chloroform (100 mL). The slurry was left stirred at r.t. for 10 min., then filtered. The filter cake was washed with methanol (3×100 mL) and the filtrate evaporated to a white solid that was dissolved in 10% aq. HCl (100 mL) and diethyl ether (50 mL). The solution was shaken and the organic layer discarded. The aqueous layer was basified to pH 14 with satd. aq. NaOH, and extracted with chloroform (3×100 mL). The organic extracts were dried over sodium sulfate and evaporated to a yellow oil that solidified (813 mg, 72%). EIMS: 154 M+.

Alternatively, these amidine intermediates can be synthesized using lithium bis(trimethylsilyl)amide:

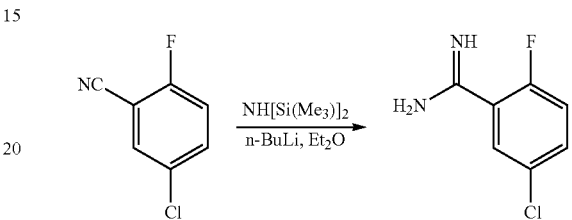

To a stirred 0° C. solution of 1,1,1,3,3,3-Hexamethyldisilazane (63 mL, 0.3 mol) in dry diethyl ether was added dropwise n-Butyl lithium (2M in hexanes, 150 mL, 0.3 mol). A white suspension formed, to which was added 2-Fluoro-5-chlorobenzonitrile (21.0 g, 0.14 mol) over 5 min. The resultant orange mixture was allowed to warm to r.t. and stirred for 2 h. The mixture was cooled to 0° C. and the reaction quenched by the addition of 3M HCl (aq.) (240 mL). The mixture was stirred for 0.5 h before water (600 mL) was added. The purple organic layer was discarded and the aqueous layer basified to pH 14 with satd. NaOH (aq.). The aqueous layer was extracted with CHCl$_3$ (5×100 mL) and the organic extracts dried over Na$_2$SO$_4$. Evaporation yielded the desired product as a yellow solid (16.2 g, 73% yield).

Compounds having no substituent at the 5-position of the pyrimidine (Y═H) can be made from the amidines by using a propiolic acid ester in place of the malonaldehyde or malonate derivatives that are typically used in Scheme 2, for example.

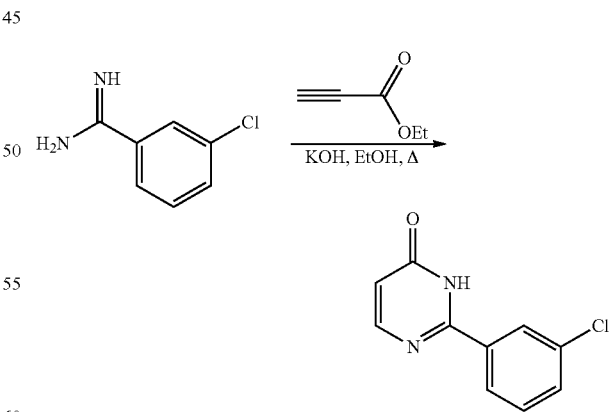

To a solution of 3-Chlorobenzamidine (1 g, 6.47 mmol) in dry ethanol (20 mL) was added ethyl propiolate (983 mL, 9.70 mmol) dropwise over 1 min. The solution was heated to 60° C. and a solution of potassium hydroxide (640 mg, 9.70 mmol) in dry ethanol (15 mL) was added dropwise over 1 h. Once added, the mixture was heated at 80° C. for 24 h, then cooled and evaporated. The residue was dissolved in water and the solution acidified with 10% aq. HCl to pH 4, whereupon a white precipitate formed, which was filtered and dried in vacuo (742 mg, 56%).

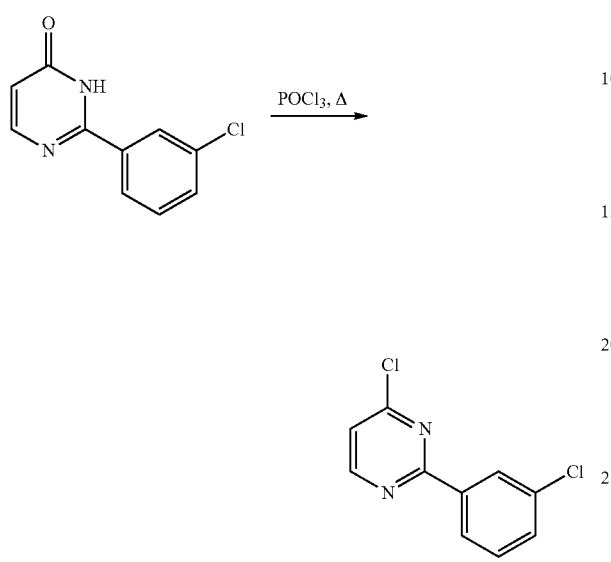

A suspension of the crude 2-(3-Chlorophenyl)-pyrimidin-4-one (197 mg, 0.9 mmol) in phosphorus oxychloride (5 mL) was heated to reflux for 0.5 h, then cooled and evaporated. The residue was purified by chromatography (eluting with CHCl₃) to yield the desired product as a white solid (191 mg, 89% yield). EIMS: 225 M+.

This intermediate can be used to make the carboxamide compounds of the invention by methods described herein: the 4-chloro substituent on the pyrimidine can be displaced by aminopyridines as described below.

Example 2

Preparation of a 2-methoxy Malonaldehyde

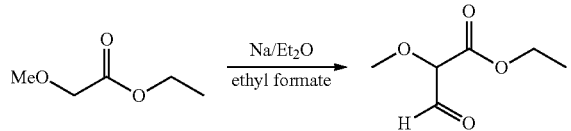

To a solution of ethyl formate (4.2 g, 56.7 mmol) in ether (80 ml) at 0° C. under N₂ was added small pieces of metal Na followed by dropwise addition of ethyl methoxy acetate (6.69 g, 56.70 mmol). The reaction was stirred for 30 min at 0° C. and was allowed to warm to ambient temperature. After 4 h at room temperature, the reaction was worked up and the product was used without further purification. The product was kept refrigerated as a stock solution.

Example 3

Preparation of 5-Isopropyl Pyrimidine Compounds

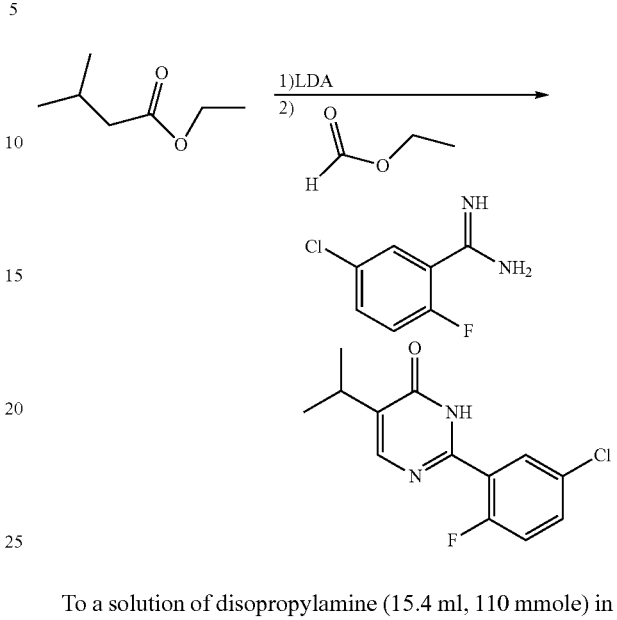

To a solution of disopropylamine (15.4 ml, 110 mmole) in 30 ml tetrahydrofuran (anh.) at −20° C. was added dropwise, n-butyllithium (2.5M hexane, 48 ml, 120 mmol). The solution was stirred at 0° C. for 40 min. The mixture was then cooled to −78° C. and ethyl isovalerate (13.0 g, 100 mmol) was added dropwise, the reaction mixture was stirred at −78° C. for 30 min. Ethyl formate (7.41 g, 100 mmol) was then added and the reaction mixture was warmed to room temperature with stirring for 1 hour. 5-chloro-2-fluorobenzamidine (17.0 g, 100 mmol) was dissolved in tetrahydrofuran (40 ml) and added to the reaction mixture over 10 min, followed by refluxing for 18 hr. Removed solvent under vacuum and residue was suspended in chloroform (150 ml) and water (150 ml). The basic aqueous phase was separated and filtered to remove some precipitate. The filtrate was acidified with glacial acetic acid to pH 5 and extracted with ethyl acetate (2×250 ml), washed combined extracts with saturated sodium chloride, dried over sodium sulfate (anh.) and removed the solvent to give 3.43 g product.

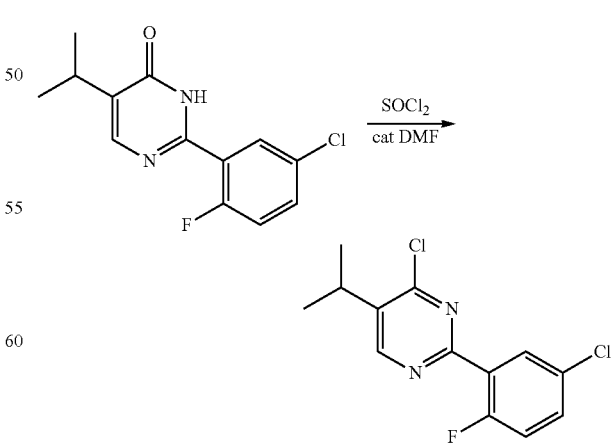

2-(5-chloro-2-fluorophenyl)-5-isopropylprimidine-4-one (3.43 g, 12.9 mmol) was suspended in thionyl chloride (15 ml, 205 mmol) and 3 drops DMF were added. The mixture was heated to 80° C. for 30 min, then excess thionyl chloride was removed under vacuum. The residue was treated with ice (50 ml) and chloroform (50 ml). Extracted product into a chloroform layer. Washed chloroform with 10% sodium carbonate (cold) and dried the chloroform layer over sodium sulfate (anh.). Solvent was then removed to give 3.32 g product.

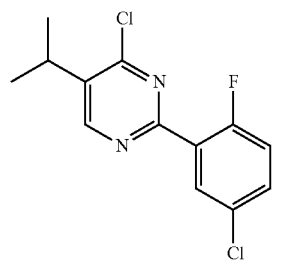
+

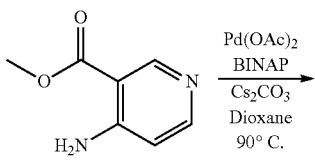

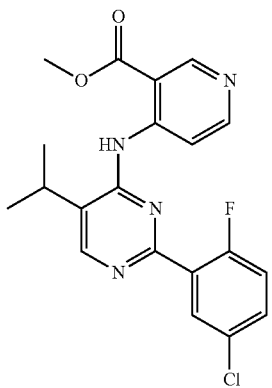

BINAP (233 mg, 0.375 mmole) and palladium(II) acetate (56.1 mg, 0.25 mmole were combined in 8 ml dioxane (anh) and heated for 5 min, followed by addition of 2-(5-chloro-2-fluorophenyl)-4-chloro-5-isoprpylpyrimidine (1.42 g, 5 mmole), methyl 4-amino-3-pyridinecarboxylate (912 mg, 6 mmole) and cesium carbonate (2.28 g, 7.0 mmole). The mixture was heated to 90° C. overnight. Removed dioxane under vacuum, the solid residue was triturated with ethyl acetate (20 ml) and filtered to give 767 mg product which contains cesium carbonate and was used directly in the next step without further purification.

Alternatively, the coupling can be achieved without using the palladium catalyst, if a stronger base is employed. This alternative is illustrated by the following example:

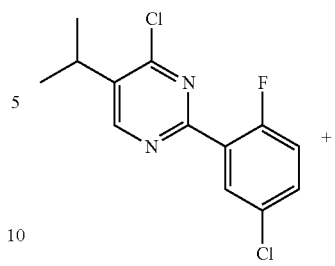
10 g
35 mmol

+

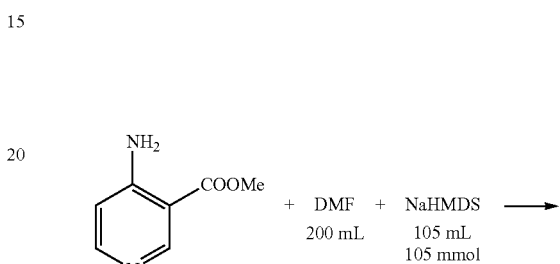
5.87 g
38.6 mmol

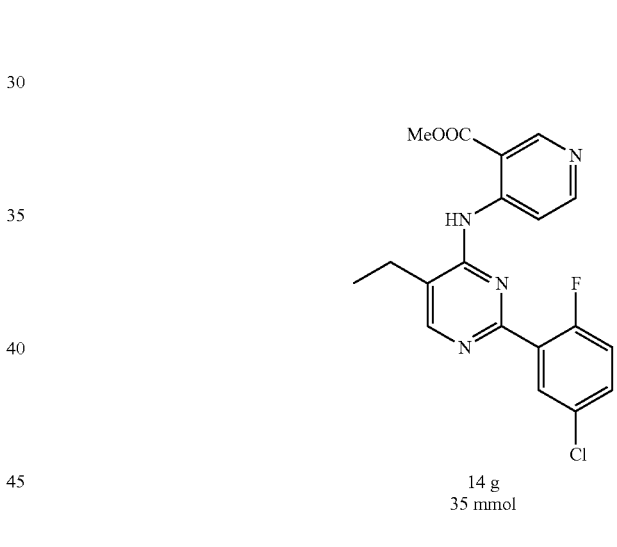
14 g
35 mmol

The chloropyrimidine (10 g, 35 mmol) and 4-amino-3-ester-pyridine (5.87 g, 38.6 mmol) were placed in an oven-dried flask (1 L), which was evacuated and flushed with nitrogen three times. Under nitrogen, anhydrous DMF (200 mL) was cannulated into the flask. Both materials were dissolved before the temperature was lowered to 0° C. Sodium hexamethyldisilazane (1M, 105 mL) in THF was then cannulated quickly into the solution. The mixture was stirred between 0° C. and 15° C. for 4 hrs. Saturated NH$_4$Cl solution (100 mL) was then added and the solvent was evaporated under vacuum. Saturated NH$_4$Cl solution (500 mL) and CH$_2$Cl$_2$ (500 mL) were then added to the crude mixture. After separation, the aqueous layer was further extracted by CH$_2$Cl$_2$ (500 mL×3). Combined organic layers were dried (Na$_2$SO$_4$), filtered and evaporated. The dark brown crude solid was triturated with 120 mL EtOAc to give light brown solid (6.66 g, 48%) as the pure desired product.

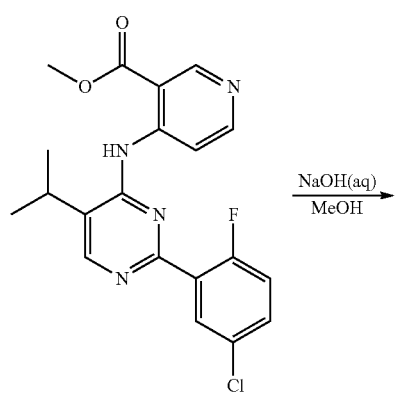

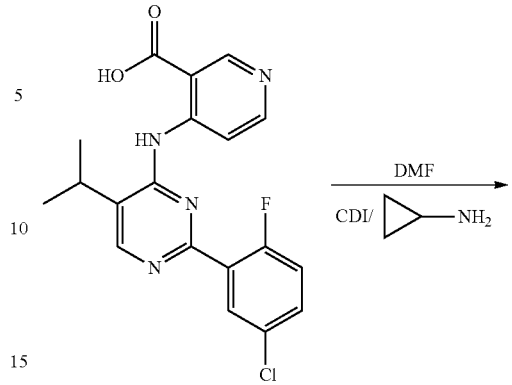

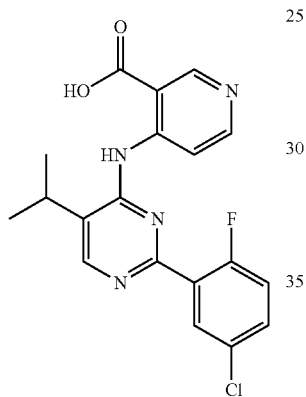

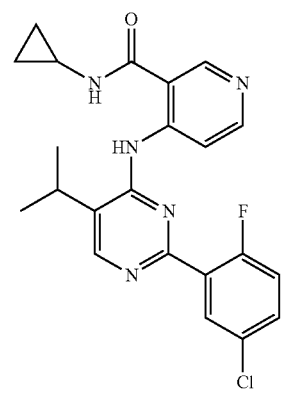

The above ester (630 mg, 1.57 mmole) was suspended in 10 ml methanol and treated with 4 ml 2.0M NaOH (aq). The mixture was refluxed for 30 min, then cooled and concentrated under vacuum to remove methanol. The aqueous solution was acidified with 6M HCl (pH 5), and filtered to obtain product; the yield was 180 mg.

The acid (193 mg, 0.5 mmole) was suspended in DMF (anh., 6 ml) and treated with carbonyl diimidazole (162 mg, 10 mmole) and heated to 60° C. for 2 hours. Cyclopropylamine (114 mg, 2.0 mmole) was added and the solution was stirred overnight at room temperature. The mixture was filtered, and the filtrate was subjected to HPLC purification. Yield: 34 mg.

Example 4

Preparation of 5-Methoxy Pyrimidine Compounds

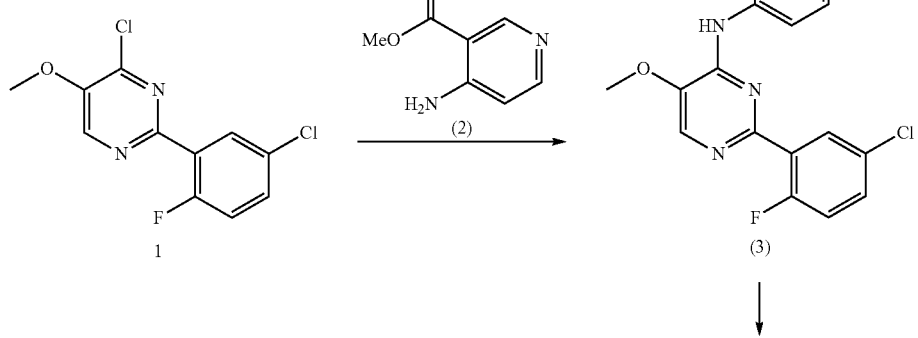

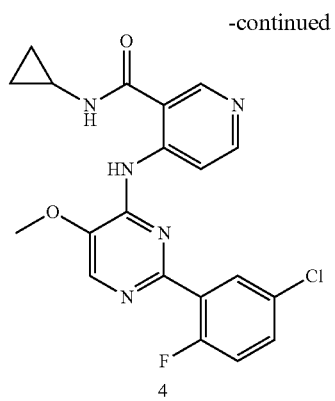
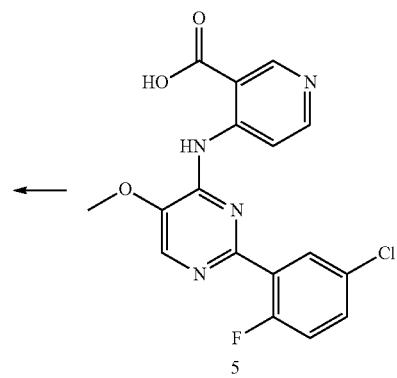

Preparation of 3:

The imino chloro compound 1 (5 g, 18.3 mmol, 1 eq), Pd$_2$(dba)$_3$ (670 mg, 0.7 mmol, 0.04 eq) and BINAP (684 mg, 1.1 mmol, 0.06 eq) were suspended in dioxane (280 mL) under inert atmosphere. A solution/suspension of the amine 2 (3.07 g, 20.2 mmol, 1.1 eq) in dioxane (90 mL) was added at a moderate speed, followed by Cs$_2$CO$_3$ (119 g, 36.5 mmol, 2 eq). The mixture was then heated to 95° C. under nitrogen for 18 hours. The warm reaction mixture was then filtered through Celite® and the Celite® pad was washed with ethyl acetate (100 mL). The filtrate was then concentrated in vacuo to approx 100 mL in volume (not to dryness). The suspension was filtered and the solid washed with ethyl acetate and dried in vacuo. Product 3 was obtained as a cream colored solid 4.92 g, 69% yield: pure.

Preparation of 4:

A suspension of the Ester 3 (1.6 g, 4.1 mmol), NaOH (1.5-1.8 eq, 0.3 g, 7.5 mmol), water (5 mL) and dioxane (50 mL) was heated to 65° C. for 0.5 hour. The reaction was cooled to room temperature and 1M HCl solution was added until a pH 4 was obtained. The suspension was filtered and washed with water. The product 4 was dried in vacuo at 40° C. overnight., 1.1 g, 71% yield (cream solid).

Preparation of 5

A suspension of the acid 4 (1 g, 2.67 mmol) and CDI (0.865 g, 5.33 mmol, 2.0 eq) in dry DMF (20 mL) was heated at 75° C. for 0.5-2 hrs under N$_2$. The reaction was cooled to room temperature and cyclopropylamine (0.3 mL, 4.1 mmol, 1.5 eq) and triethylamine (0.4 mL, 2.67 mmol) were added. The reaction was stirred for 18 hours. The reaction mixture was then filtered and the solid washed with ethyl acetate. The pure product was obtained as a white solid, 0.71 g, 65% yield.

Example 5

Preparation of Compounds with a 5-Cyclopropyl Pyrimidine

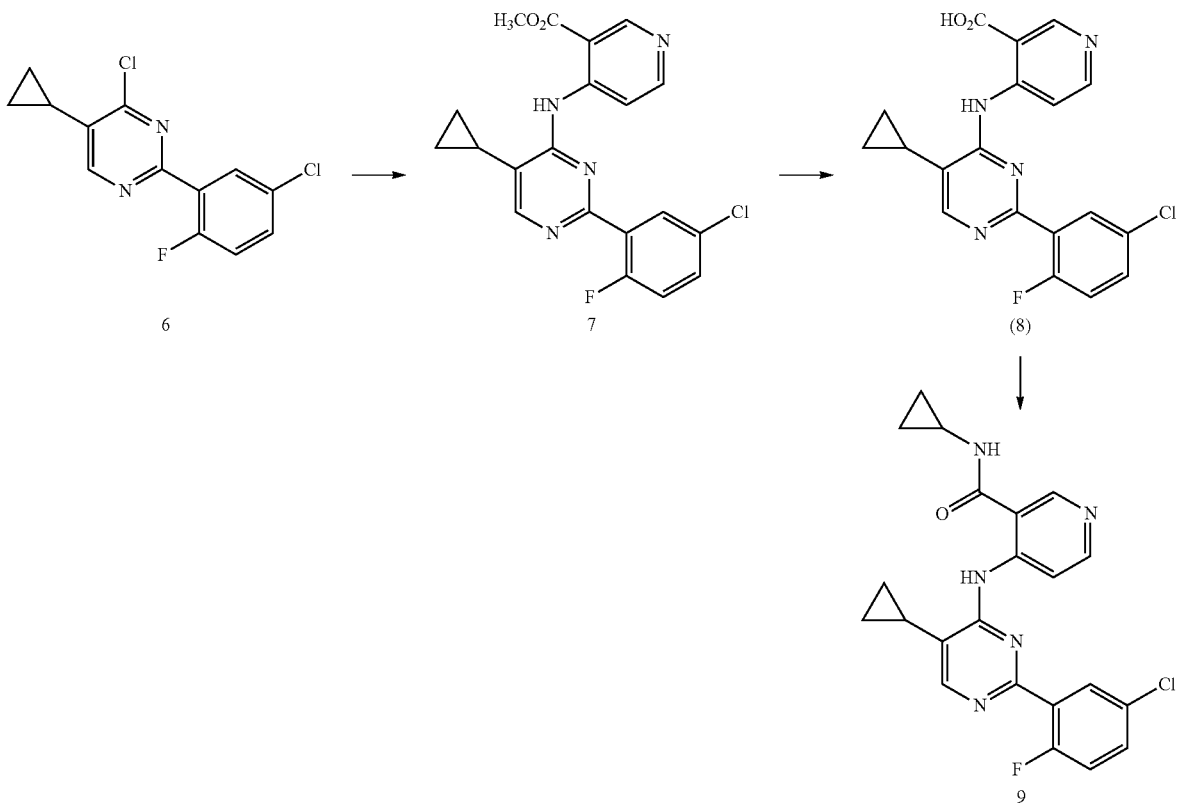

Preparation of 7:

To 1.42 g (5.0 mmol) of (6), was added 2.2 g (7.0 mmol) cesium carbonate, 0.056 g (0.25 mmol) Pd(OAc)$_2$, 0.233 g (0.44 mmol) BINAP, and 0.912 g (6.0 mmol) of 4-amino-3-methylester pyridine. 10 ml of anhydrous 1-4-dioxane was added and the mixture was heated to 90° C. overnight. Dioxane was removed by reduced pressure and material was washed with ethylacetate.

Preparation of 8:

To 0.35 g (1.24 mmol) of (7) was added 8 ml of methanol and 3 ml of a 1M NaOH solution. Mixture was heated to 70° C. for 2 hrs, cooled then acidified to pH5 using 1M HCl. Product was collected by vacuum filtration, washed with a small amount of water and dried in vacuum oven.

Preparation of 9:

To 0.223 g (0.589 mmol) of (8), was added 0.19 g (0.18 mmol) of N,N'-carbonyldiimidazole. The mixture was treated with 4 ml of anhydrous DMF and heated to 70° C. for 2 hrs. Reaction was cooled to room temperature and 0.168 g (2.9 mmol) of cyclopropylamine was added and the reaction stirred at room temperature overnight. Reaction was then filtered and purified by prep HPLC.

Example 6

Preparation of a 5-Cyclobutyl Pyrimidine Compound

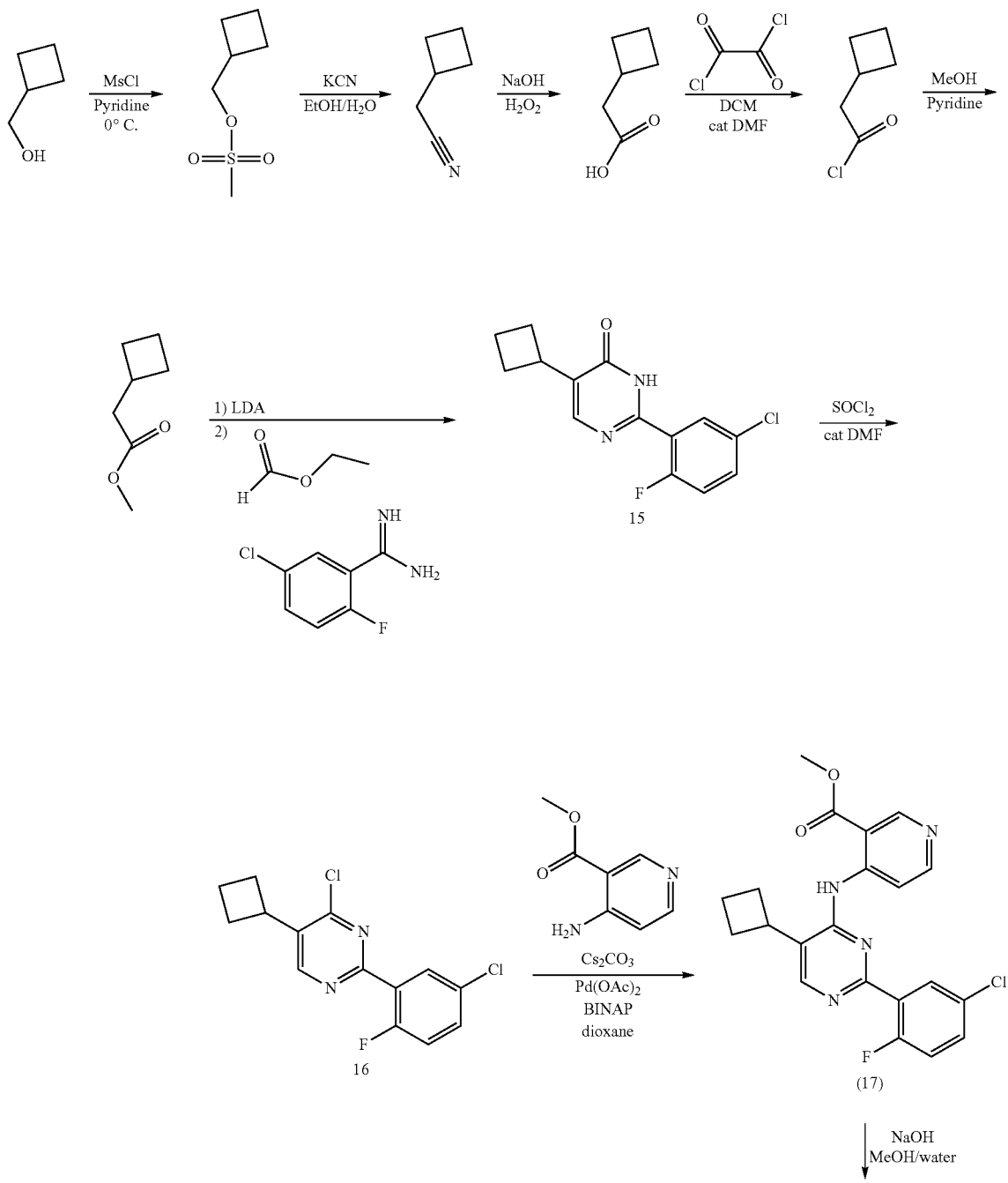

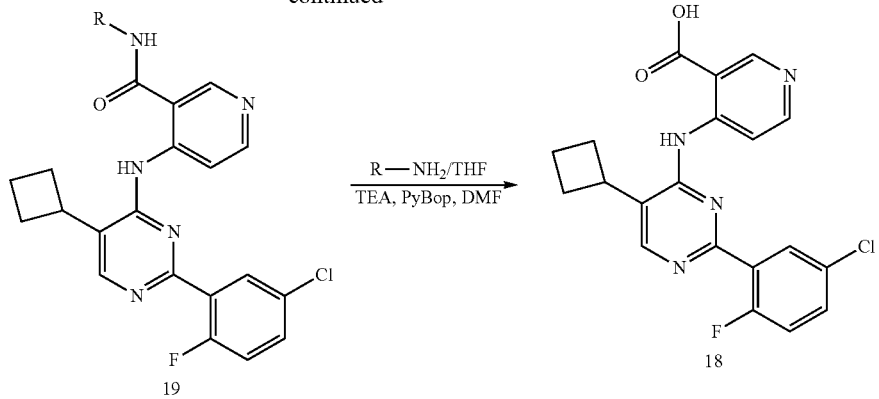

Preparation of Methyl Cyclobutylacetate:

A mixture of cyclobutylmethanol (25 g, 0.290 mole) and methanesulfonyl chloride (33.25 g, 0.290 mole) was stirred at 0° C. while pyridine was added drop wise over 2.5 hours. Reaction mixture was kept at 0° C. overnight, then combined with 150 ml ice cold 10% HCl. The mixture was extracted with diethyl ether (3×125 ml). Combined extracts were washed with water (2×20 ml) followed by saturated sodium bicarbonate (30 ml). Dried extract over anhydrous sodium sulfate and solvent removed under reduced pressure to give 35.58 g product.

Cyclobutymethylmesylate (35.38 g 0.215 mole) was dissolved in 250 ml 80% ethanol/water and treated with potassium cyanide (25.25 g, 0.388, 1.8 eq) and the reaction mixture was refluxed overnight. Poured reaction mixture into 200 ml water and extracted with diethyl ether (2×100 ml), then washed with saturated sodium chloride (~50 ml). Dried ether over sodium sulfate (anh.). The dark brown solution was passed over Florisil® (~10 cm I.D.×15 cm) twice to remove brown color. Removal of solvent gave crude product, which was purified further by vacuum distillation to give 9.5 g product.

An ice cooled bath of sodium hydroxide (40 g) in 50 ml water was stirred while a 30% hydrogen peroxide solution (50 ml) was added slowly maintaining cool temperature. Cyclobutylacetonitrile (9.5 g, 0.10 mole) was added slowly, and the solution was stirred 30 min then heated to reflux for 2 days. Cooled reaction mixture, extracted with 50 ml chloroform to remove unreacted nitrile. Acidified aqueous layer with conc. HCl to pH 2, extracted cooled mixture with chloroform (3×150 ml). Dried chloroform extract over magnesium sulfate (anh.). Evaporated solvent to give 8.63 g product.

Cyclobutylacetic acid (8.63 g, 75.6 mmole) was dissolved in dichloromethane containing 2 drops dimethylformamide, and oxalyl chloride (45 ml, 2M in dichloromethane) was added drop wise over 30 min at room temperature. The reaction mixture was stirred at room temperature for 3 hours, and then solvent removed to give 8.6 g product.

Cyclobutyl acetyl chloride (8.6 g, 64.8 mmole) was added dropwise to a stirred solution of pyridine (10.48 ml, 129.6 mmole) in methanol (105 ml). The solution was stirred overnight at room temperature. Most of the excess methanol was removed under vacuum. Solution was poured onto 150 ml water, extracted with diethyl ether (3×125 ml). Combined extracts were washed with 25 ml 10% HCl, water (25 ml) and saturated sodium bicarbonate (25 ml), water (25 ml), saturated sodium chloride (25 ml).

Ether was dried over anhydrous sodium sulfate and solvent removed to give 5.90 g methyl cyclobutylacetate.

Preparation of 15:

To a solution of diisopropylamine (7.15 ml, 50.63 mmol) in 20 ml anhydrous tetrahydrofuran at −20° C., was added n-butyl lithium (2.5M hexanes, 22 ml, 55.23 mmol) dropwise. The solution was stirred at 0° C. for 40 min, and cooled reaction to −78° C. Methyl cyclobutyl acetate (5.9 g, 46.03 mmol) was added dropwise, and the reaction mixture was stirred at −78° C. for 30 min. Ethyl formate (3.71 ml, 46.03 mmol) was added and reaction mixture was warmed to −10° C. for 1 hour, then room temp 1 hour. 5-chloro-2-fluorobenzamidine (7.94 g, 46.03 mmol) was dissolved in 20 ml tetrahydrofuran and added to the reaction mixture dropwise over 10 min. The mixture was then refluxed overnight. Removed most of the tetrahydrofuran under vacuum, and residue was taken up in 200 ml water. Washed aqueous solution with diethyl ether (2×75 ml) which removed dark color. Aqueous phase was acidified with glacial acetic acid to pH 5. Product precipitated from solution. Filtered solid, washed with water and vacuum dried to give 3.77 g product. (29% yield).

Preparation of 16:

2-(5-chloro-2-fluoro)-5-cyclobutylpyrimidine-4-one (3.75 g, 13.5 mmole) was suspended in thionyl chloride (15 ml, 205 mmole), added 2 drops dimethylformamide and heated mixture to 80° C. for 30 min. Starting material was completed dissolved at this time. Removed excess thionyl chloride under vacuum and residue was poured onto ice water and extracted with chloroform. The chloroform layer was washed with 10% sodium carbonate, and dried over anhydrous. Filtration and solvent removal give 3.98 g product. (99%).

Preparation of 17:

2-(5-chloro-2-fluoro)-4-chloro-5-cyclobutylpyrimidine (1.48 g, 5 mmol), cesium carbonate (2.28 g, 7 mmol), palladium(II) acetate (56.1 mg, 0.25 mmol), BINAP (233 mg, 0.375 mmol) and methyl 4-aminopyridine-3-carboxylate (912 mg, 6 mmol) were combined in dioxane and heated to 80° C. overnight. Removed solvent under vacuum, triturated residue with ethyl acetate, filtered solid, washed with ethyl acetate to give 4.20 g solid, estimated to contain 1.92 g product, along with remaining cesium carbonate. This material was used directly without further purification.

Preparation of 18:

The above crude material (4.20 g, estimated to contain 1.92 g starting material+cesium carbonate) was suspended in methanol 10 ml, and 10 ml M sodium hydroxide was added. Refluxed the solution for 1 hour, then cooled mixture, removed methanol under vacuum, acidified aqueous solution to pH 4 with 1M HCl, filtered solid washing with water to give 1.30 g product after vacuum oven drying.

Preparation of 19:

Compound 18 (130 mg, 0.326 mmole) was suspended in dimethylformamide (8 ml). To this was added Pybop (254 mg, 0.489 mmole), triethylamine (49 microliters, 0.359 mmole) and 2M methyl amine/THF (815 microliters, 1.63 mmole) and the reaction was stirred at room temperature for 3 hours. The reaction mixture was filtered through 0.45 micron filter and subjected to HPLC purification to give 61 mg product.

Example 7

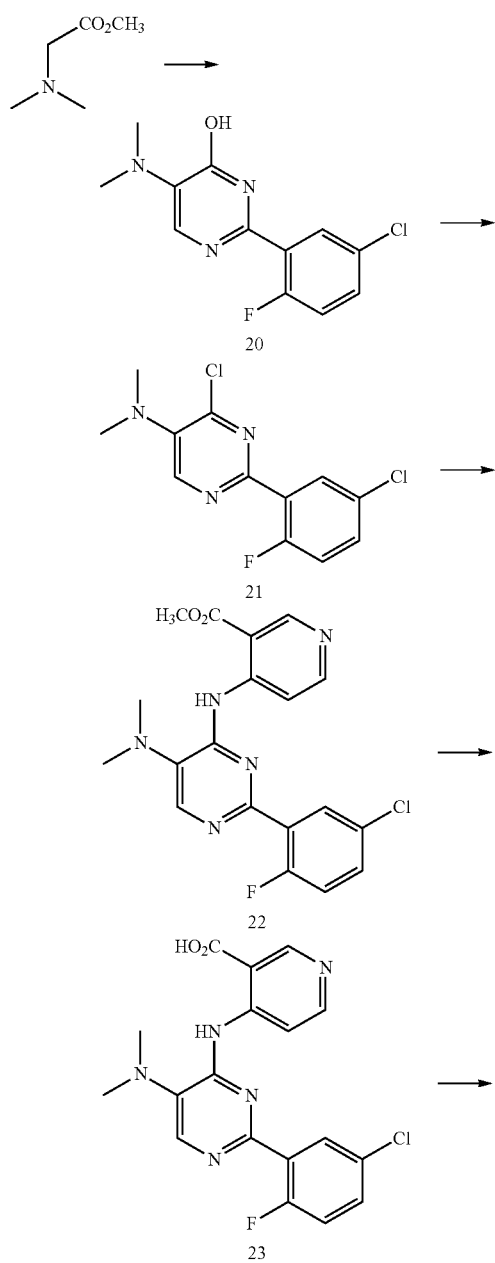

Preparation of 20:

Solid sodium metal pieces (2.11 g, 92.0 mmol) were washed with hexane and crushed into smaller pieces. Hexane was removed and the sodium pieces were added to a stirred solution at 0° C. of N,N-dimethylglycine methyl ester, (10.78 g, 92.0 mmol in anhydrous ether (80 ml)). Ethyl formate (7.4 ml, 92.0 mmol) was added dropwise to this solution and the reaction was stirred at room temperature for 3 hours. The reaction solution turned a creamy yellow consistency. To this mixture, 5-chloro-2-fluorobenzamidine, (15.9 g, 92.0 mmol) dissolved in 100 ml of 200 proof ethanol was syringed into the reaction flask and the mixture was refluxed gently overnight. Solvent was then removed under reduced pressure and slurry was taken up into chloroform and extracted with water. The aqueous layer was adjusted to pH 7 and extracted with chloroform. Combined organic solvent was dried using magnesium sulfate and concentrated. Crude product was then washed with 20% ethyl acetate/Hexane. Yield is 4.3 g, 17.5%.

Preparation of 21:

2-(5-chloro-2-fluorobenzyl)-5-cyclopropyl-pyrimidone, (0.46 g, 1.61 mmol) was treated with (2 ml, 15.7 mmol) of phosphorus oxychloride and refluxed for 2 hrs. Solvent was removed under reduced pressure and product was extracted into chloroform and washed with a saturated solution of sodium hydrogen carbonate cooled with ice. Organic solvent was dried using magnesium sulfate and concentrated. Reaction produced 0.43 g of product, 95% yield.

Preparation of 22:

Imino chloride (21), (0.43 g, 1.5 mmol) was dissolved in 5 ml of anhydrous 1,4-dioxane. To this (0.29 g, 1.9 mmol) of 5, (0.018 g, 0.080 mmol) of palladium acetate, (0.075 g, 0.121 mmol) of BINAP, and (0.786 g, 2.41 mmol) of cesium carbonate were added at once. The reaction was refluxed for 3 hours, cooled and the dioxane was evaporated off. Crude product was washed with ethyl acetate. The crude product was mixed with cesium carbonate. No yield was taken.

Preparation of 23:

To (22) was added 15 ml of methanol and 3 ml of a 1M NaOH solution. Mixture was heated to 70° C. for 2 hrs, cooled then acidified to pH4 using 1M HCl. Product was collected by vacuum filtration, washed with a small amount of water and dried in vacuum oven. Received 0.064 g, 10.3% collective yield from imino chloride (21).

Preparation of 24:

To (0.064 g, 0.166 mmol) of (23), was added (0.054 g, 0.330 mmol) of N,N'-Carbonyldiimidazole. The mixture was treated with 5 ml of anhydrous DMF and heated to 70° C. for 2 hrs. Reaction was cooled to room temperature and 0.249 ml (0.498 mmol) of methylamine was added and the reaction stirred at room temperature overnight. Reaction was then filtered and purified by prep HPLC. Received 0.0152 g of material, 22.7% yield.

Example 8

Preparation of a 5-Benzyloxy Pyrimidine Compound stirred at −78° C. for 30 min. Ethyl formate (13.70 g, 185 mmol) was then added and the reaction mixture was warmed to room temperature with stirring for 18 hours. The reaction mixture was poured into 300 ml ice water. The organic layer was extracted with 1M sodium hydroxide (2×40 ml) and added to the aqueous layer. The aqueous layer was acidified with 40% sulfuric acid to pH 5.0 with cooling. The solution was extracted with diethyl ether (5×40 ml), combined ether

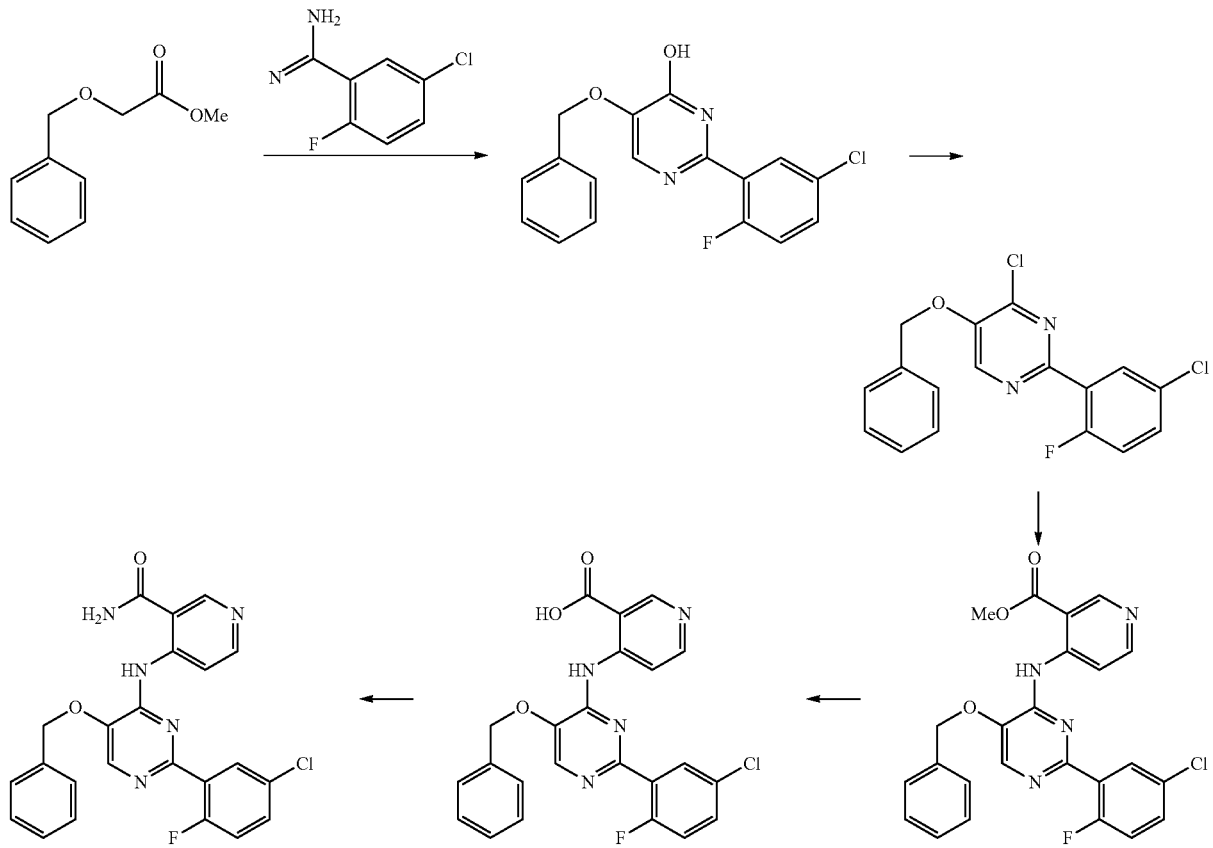

The 5-benzyloxy analogs were synthesized using the same conditions as those for the 5-methoxy analogs, but using methyl-benzyloxyacetate 31 as the starting material.

extract washed with saturated sodium chloride, dried over sodium sulfate (anh.) and solvent removed to give product as a liquid (11.4 g, 39% yield). This material was used without further purification.

Example 9

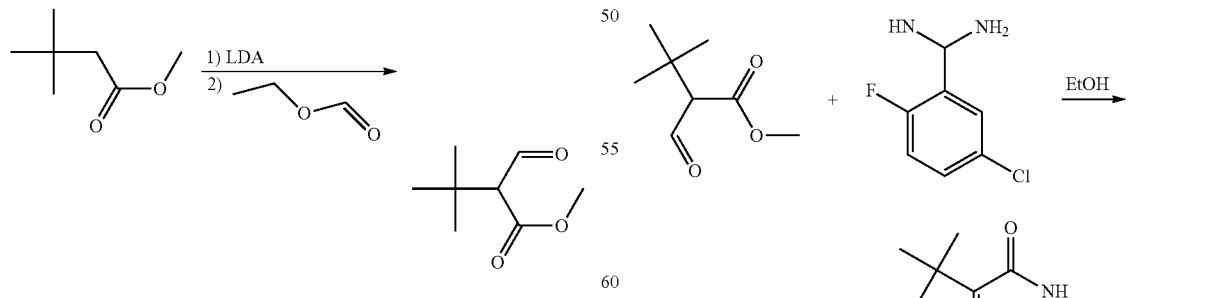

To a solution of diisopropylamine (20.58 g, 204 mmole) in 60 ml tetrahydrofuran (anh.) at −20° C. was added dropwise, n-butyllithium (2.5M hexane, 88 ml, 222 mmol). The solution was stirred at 0° C. for 40 min. The mixture was then cooled to −78° C. and methyl t-butyl acetate (24.1 g, 185 mmol) was added dropwise, the reaction mixture was 5-chloro-2-fluorobenzamidine (7.39 g, 42.8 mmole) and methyl 1-formyl-t-butyl acetate (6.78 g, 42.8 mmole) were dissolved in ethanol (75 ml) and heated to reflux for 2 hours. Removed ethanol by rotary evaporation; the residue was taken up in chloroform (300 ml), and was extracted with 1M sodium hydroxide (4×40 ml). Combined aqueous extract was acidified with 1M hydrochloric acid. Product was extracted with ethyl acetate (3×100 ml), the combined extract was dried over sodium sulfate (anh.) and the solvent removed to give the product 2.02 g (17% yield).

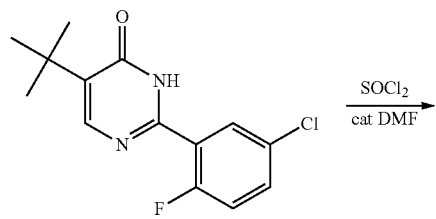

2-(5-chloro-2-fluorophenyl)-5-t-butylprimidine-4-one (2.02, 7.20 mmole) was suspended in thionyl chloride (10 ml) and 3 drops DMF were added. The mixture was heated to 80° C. for 30 min, removed excess thionyl chloride under vacuum. The residue was treated with ice (50 ml) and chloroform (50 ml). Extracted product into chloroform. Washed chloroform with 10% sodium carbonate (cold) and dried chloroform layer over sodium sulfate (anh.) Removed solvent to give 2.00 g product. (93% yield).

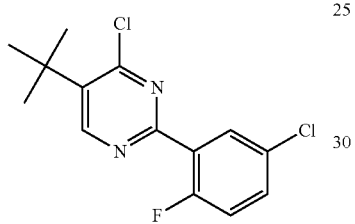

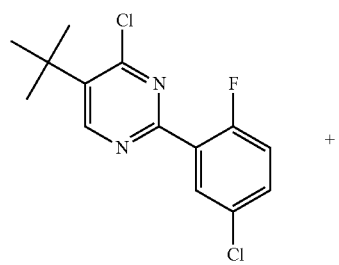

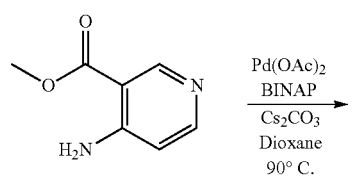

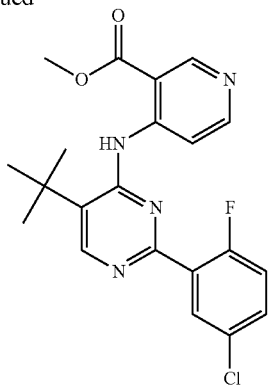

BINAP (311 mg, 0.50 mmol) and palladium(II) acetate (74 mg, 0.334 mmol were combined in 10 ml dioxane (anh.) and heated for 5 min, followed by addition of 2-(5-chloro-2-fluorophenyl)-4-chloro-5-t-butyllpyrimidine (2.00 g, 6.68 mmol), methyl 4-amino-3-pyridinecarboxylate (1.22 g, 8.0 mmol) and cesium carbonate (3.05 g, 9.38 mmol). The mixture was heated to 90° C. overnight. Removed dioxane under vacuum, the solid residue was triturated with ethyl acetate (20 ml) and filtered to give 3.15 g product which contains cesium carbonate and was used directly in next step without further purification.

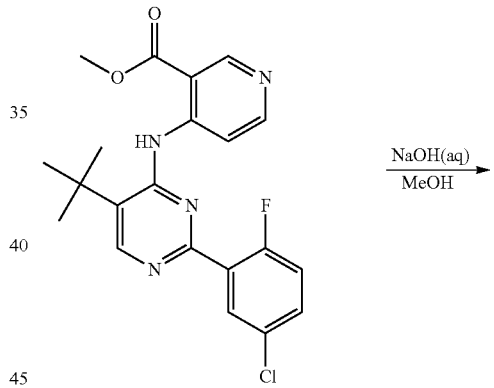

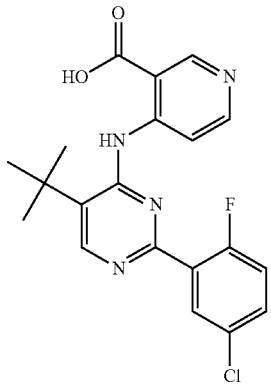

The ester (3.15 g,) was suspended in 10 ml methanol and treated with 4 ml 2.0M NaOH (aq). The mixture was refluxed for 1 hour, then the cooled reaction mixture was concentrated under vacuum to remove methanol. The aqueous solution was acidified with 6M HCl (pH 5), and filtered to obtain product 2.25 g.

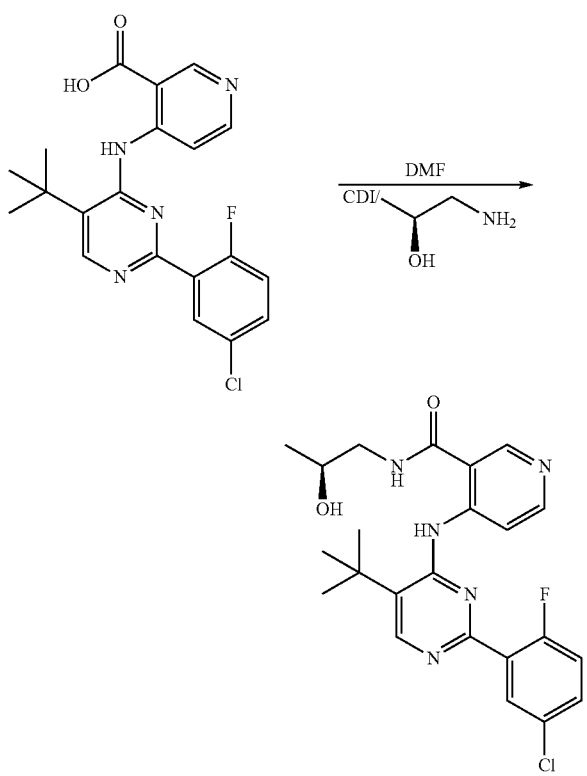

The acid (100 mg, 0.25 mmole) was suspended in DMF (anh., 3 ml) and treated with carbonyl diimidazole (81 mg, 0.5 mmole) and heated to 60° C. for 2 hours. S(+)-1-amino-2-propanol (75 mg, 1.0 mmole) was added and the solution was stirred overnight at room temperature. Filtered the mixture, and the filtrate was subjected to HPLC purification. Isolated 12 mg product.

Example 10

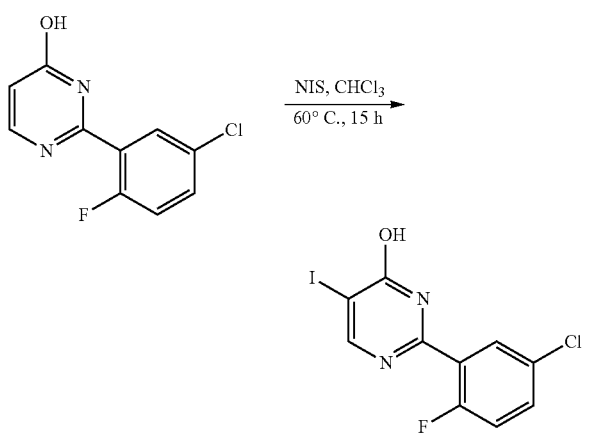

2-(5-Chloro-2-fluorophenyl)-5-iodopyrimidin-4-ol

To a solution of pyrimidone, 2-(5-chloro-2-fluorophenyl)-pyrimidin-4-ol (3.65 g, 16 mmol, 1 eq), in dry chloroform was added N-halosuccinimide, NIS (5.5 g, 24 mmol, 1.5 eq) in one portion and the reaction mixture was heated to 60° C. overnight. The reaction mixture was cooled to rt and partitioned between chloroform and water. The organic layers were combined, washed with brine, dried over MgSO$_4$, filtered and concentrated in vacuo and the residue was purified by flash column chromatography to give 2-(5-Chloro-2-fluoro-phenyl)-5-iodopyrimidin-4-ol (4.82 g, 84%) as a cream colored solid.

The product was converted into a compound of formula (I) by the methods in Example 3 above.

Example 11

2-Cyclopentyl-3-oxo-propionic Acid Methyl Ester

To a solution of diisopropylamine (18.92 g, 0.135 mole) in tetrahydrofuran (40 ml) at −20° C. was added n-butyl lithium (2.5M hexanes, 59 ml, 0.147 mole) dropwise. The solution stirred for 40 minutes at 0° C. The mixture was cooled to −78° C. and cyclopentyl-acetic acid methyl ester (17.52 g, 0.123 mole) was added dropwise. The reaction mixture continued to stir at −78° C. for 30 min. Ethyl formate 9.66 ml., 0.123 mole) was added and the reaction mixture was allowed to warm to room temperature while stirring for 18 hours. The reaction mixture was poured into ice water (300 ml). The organic phase was extracted with sodium hydroxide (1M, 2×40 ml) and the aqueous layers were combined. The cooled aqueous solution was acidified with 40% sulfuric acid to pH. The mixture was extracted with diethyl ether (5×40 ml), and the combined extracts were washed with saturated sodium chloride solution, and dried over anhydrous sodium sulfate. The organic solvent was removed under reduced pressure to give a 2-Cyclopentyl-3-oxo-propionic acid methyl ester as slightly yellow liquid, 16.24 g (78% yield). This material was used in the next step without further purification.

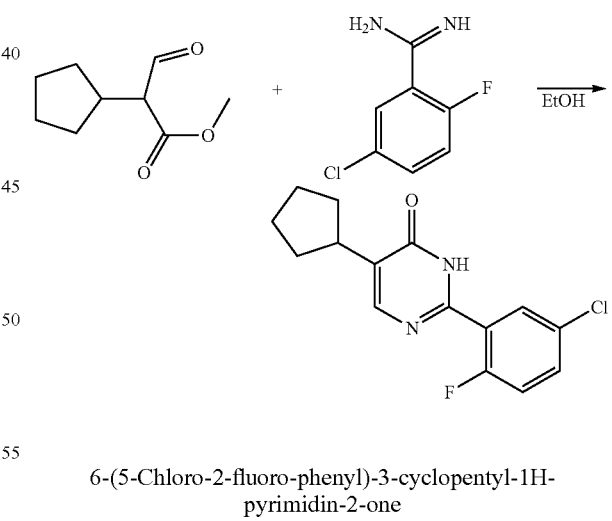

6-(5-Chloro-2-fluoro-phenyl)-3-cyclopentyl-1H-pyrimidin-2-one

The betaaldehyde ester, 2-Cyclopentyl-3-oxo-propionic acid methyl ester (16.24 g, 95 mmol) and benzamidine, 5-chloro-2-fluorobenzamidine (16.39 g, 95 mmol) were combined in ethanol (120 ml) and heated to 80° C. for 18 hours. Ethanol was removed under reduced pressure and chloroform (400 mL) was added followed by 1M sodium hydroxide (100 ml). The aqueous layer was washed with chloroform (2×50 ml), acidified with 1M hydrochloric acid and extracted with ethyl acetate. Much of the product solidified from solution and was isolated by filtration. Upon drying the ethyl acetate filtrate further 6-(5-Chloro-2-fluoro-phenyl)-3-cyclopentyl-1Hpyrimidin-2-one was obtained after removal of the solvent under reduced pressure to afford 14.37 g (51% yield).

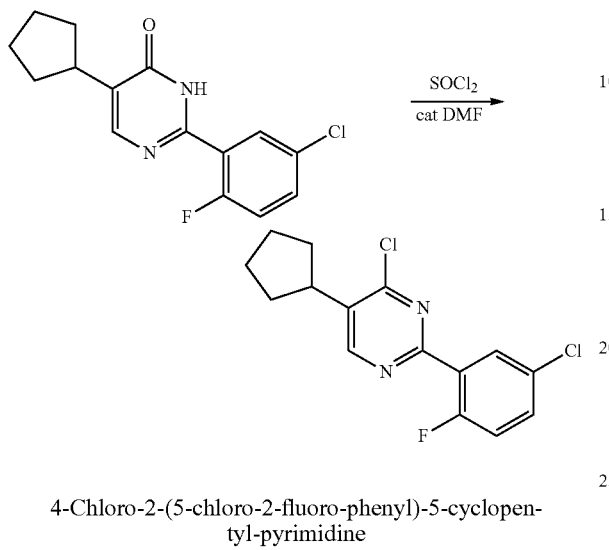

4-Chloro-2-(5-chloro-2-fluoro-phenyl)-5-cyclopen-tyl-pyrimidine

Pyrimidone, 6-(5-Chloro-2-fluoro-phenyl)-3-cyclopen-tyl-1H-pyridin-2-one (4.95 g, 16.91 mmole) was treated with thionyl chloride (20 ml). Dimethylformamide (3 drops) was added and the mixture was heated to reflux for 45 minutes. Excess thionyl chloide was removed under reduced pressure and the residue was combined with ice (~100 g), chloroform (100 ml) and extracted product into chloroform layer. The chloroform extract was washed with 10% sodium carbonate, dried over anhydrous sodium sulfate and the solvent was removed under reduced pressure. This material was further purified by column chromatography over silica gel (chloroform). Obtained 4-Chloro-2-(5-chloro-2-fluoro-phenyl)-5-cyclopentyl-pyrimidine (5.00 g, Yield: 95%).

The compounds prepared by the methods described above can, of course, be further modified using methods known in the art. The following examples illustrate particular embodiments of such further transformations, but are offered as examples only and in no way limit the scope of the invention.

Example 12

Derivatization of Compounds Made by the Preceding Methods

Synthesis of 4-[2-(5-Chloro-2-fluoro-phenyl)-5-methoxy-pyrimidin-4-ylamino]-N-[3-(3-isopropyl-ureido)-propyl]-nicotinamide

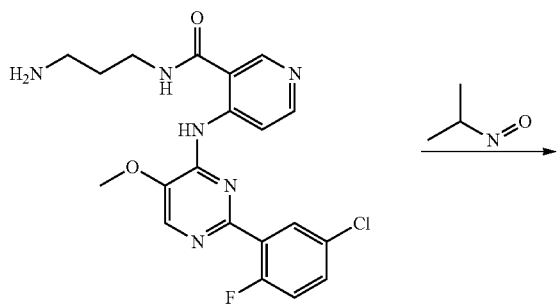

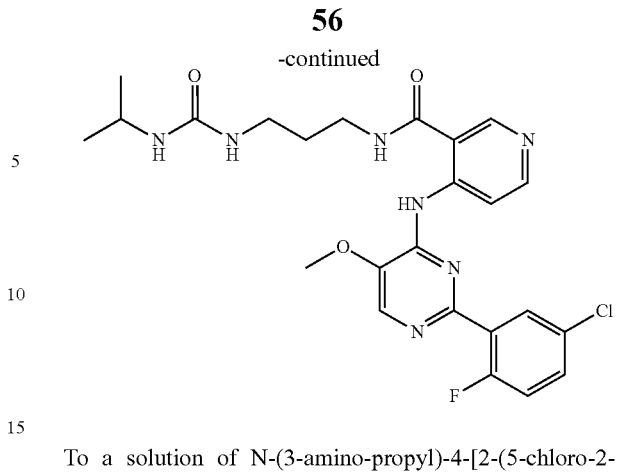

To a solution of N-(3-amino-propyl)-4-[2-(5-chloro-2-fluoro-phenyl)-5-methoxypyrimidin-4-ylamino]-nicotinamide (50 mg, 0.1163 mmol) in EtOAc (5 ml) was added triethyl amine (17 ul, 0.1163 mmol) and isoproyl isocyanate (0.1163 mmol). The reaction solution was stirred at room temperature overnight and a precipitate formed. The solvent was removed in vacu and the solid residue was rinsed with MeOH. 4-[2-(5-Chloro-2-fluoro-phenyl)-5-methoxy-py-rimidin-4-ylamino]-N-[3-(3-isopropyl-ureido)-propyl]-nicotinamide (20 mg) was obtained as a solid.

Example 13

Synthesis of 4-[2-(5-Chloro-2-fluoro-phenyl)-5-methoxy-pyrimidin-4-ylamino]-N-[3-(2-methylbu-tyrylamino)-propyl]-nicotinamide

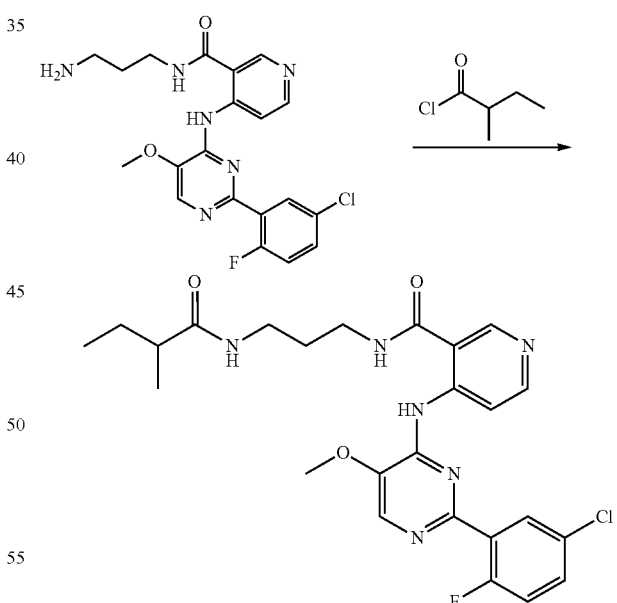

4-[2-(5-Chloro-2-fluoro-phenyl)-5-methoxy-pyrimi-din-4-ylamino]-N-[3-(2-methyl-butyrylamino)-pro-pyl]-nicotinamide To solution of N-(3-amino-propyl)-4-[2-(5-chloro-2-fluoro-phenyl)-5-methoxy-pyrimidin-4-ylamino]-nicotina-mide (50 mg, 0.1163 mmol) in DMF (5 ml) was added isobutyryl chloride (24 ul, 0.2326 mmol). The reaction solution was stirred at ambient temperature overnight. The product was purified by prep HPLC after removal of solvent to afford 4-[2-(5-chloro-2-fluoro-phenyl)-5-methoxy-pyrimidin-4-ylamino]-N-[3-(2-methyl-butyrylamino)-propyl]-nicotinamide (16% yield).

Example 14

Synthesis of 4-[2-(5-chloro-2-fluoro-phenyl)-5-methoxy-5,6-dihydro-pyrimidin-4-yl-amino]-N-{3-[(cyanoimino-isopropylamino-methylene)-amino]-propyl}-nicotinamide

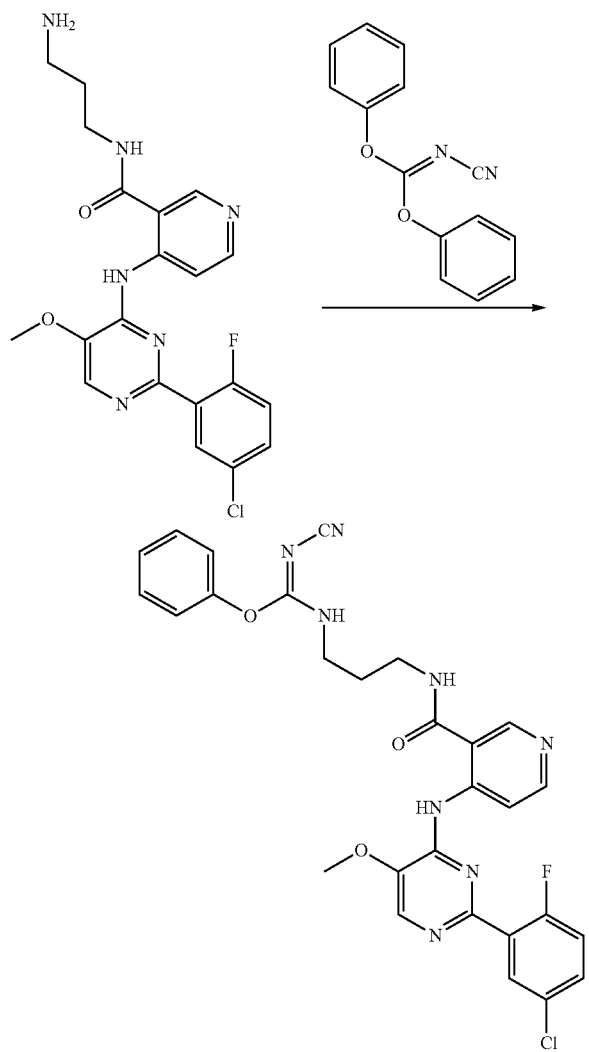

4-[2-(5-Chloro-2-fluoro-phenyl)-5-methoxy-5,6-dihydro-pyrimidin-4-ylamino]-N-{3-[(cyanoimino-phenoxy-methylene)-amino]-propyl}-nicotinamide The N-(3-aminopropyl)-4-[2-(5-chloro-2-fluoro-phenyl)-5-methoxy-5,6-dihydro-pyrimidin-4-ylamino]-nicotinamide (0.200 g) was dissolved in 2-propanol (20 mL) and diphenoxymethylenecyanamine (0.115) was added. The mixture stirred at 70° C. for 8 h and then was cooled to rt. The mixture was filtered and the solid material was filtered 4-[2-(5-chloro-2-fluoro-phenyl)-5-methoxy-5,6-dihydro-pyrimidin-4-ylamino]-N-{3-[(cyanoimino-phenoxy-methylene)-amino]-propyl}-nicotinamide (0.160 mg) and used in the next reaction without further purification.

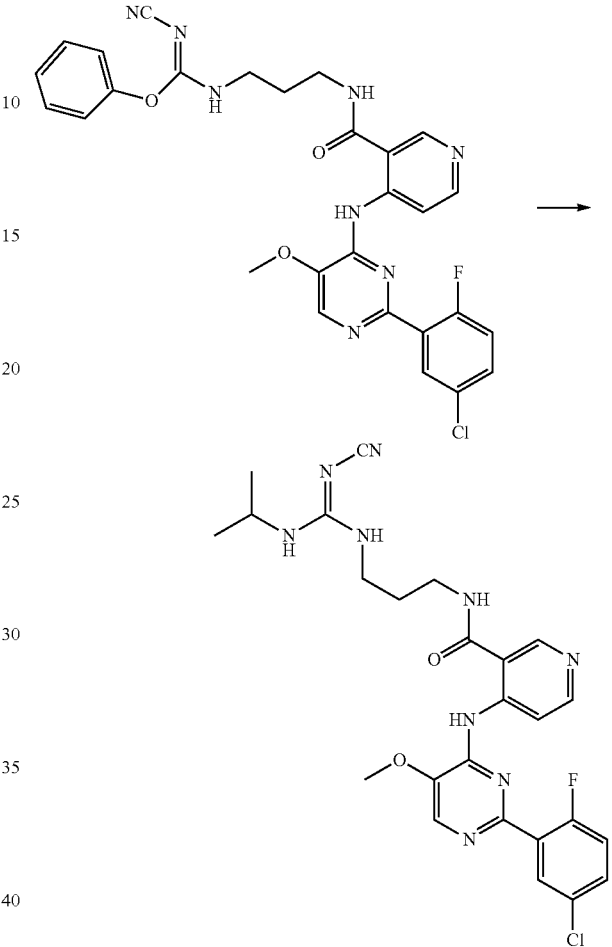

4-[2-(5-Chloro-2-fluoro-phenyl)-5-methoxy-5,6-dihydro-pyrimidin-4-ylamino]-N-{3-[(cyanoimino-isopropylamino-methylene)-amino]-propyl}-nicotinamide To a solution of collected 4-[2-(5-chloro-2-fluoro-phenyl)-5-methoxy-5,6-dihydro-pyrimidin-4-ylamino]-N-{3-[(cyanoimino-phenoxy-methylene)-amino]-propyl}-nicotinamide (0.050 g) in 2-propanol (5 mL) was added iso-propyl amine (5 equivalents). The mixture stirred at rt for 5 days in a sealed flask. The reaction was reduced in volume and filtered to afford the desired product 4-[2-(5-chloro-2-fluoro-phenyl)-5-methoxy-5,6-dihydro-pyrimidin-4-ylamino]-N-{3-[(cyanoimino-isopropylamino-methylene)-amino]-propyl}-nicotinamide (3.7 mg).

Example 15

4-({4-[2-(5-Chloro-2-fluoro-phenyl)-5-methoxy-pyrimidin-4-ylamino]-pyridine-3-carbonyl}-amino)-pyrrolidine-1,2-dicarboxylic acid 1-tert-butyl ester 2-methyl ester Synthesized as described in Example 3, using N1-BOC protected 4-aminoproline methyl ester.

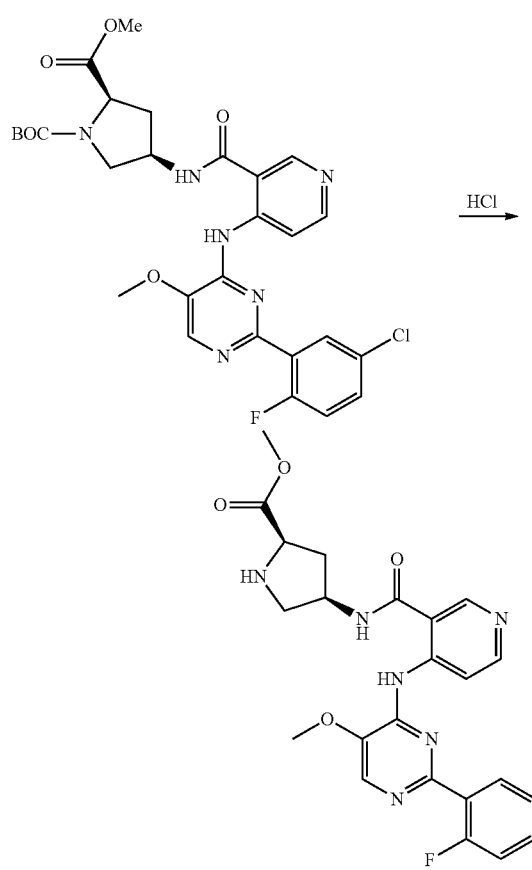

4-({4-[2-(5-Chloro-2-fluoro-phenyl)-5-methoxy-pyrimidin-4-ylamino]-pyridine-3-carbonyl}-amino)-pyrrolidine-2-carboxylic acid methyl ester The BOC-protected amine, 4-({4-[2-(5-chloro-2-fluoro-phenyl)-5-methoxy-pyrimidin-4-ylamino]-pyridine-3-carbonyl}-amino)-pyrrolidine-1,2-dicarboxylic acid 1-tert-butyl ester 2-methyl ester (50 mg) in 4M HCL dioxane (2 mL) was stirred for 4 hours. The solvent was removed in vacuo. Purification by preparative HPLC (5/70 water/acetonitrile/ 20 mins) afforded 4-({4-[2-(5-chloro-2-fluoro-phenyl)-5-methoxy-pyrimidin-4-ylamino]-pyridine-3-carbonyl}-amino)-pyrrolidine-2-carboxylic acid methyl ester (25 mg, 0.050 mmol; 50% yield).

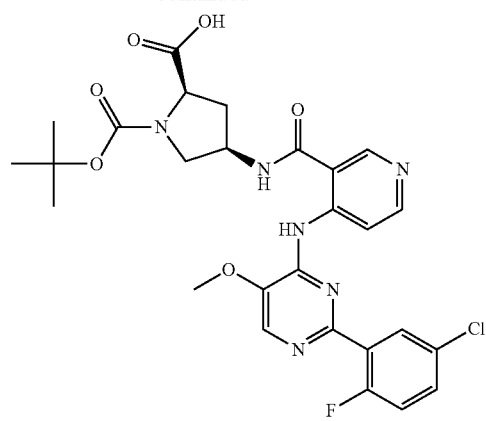

4-({4-[2-(5-Chloro-2-fluoro-phenyl)-5-methoxy-pyrimidin-4-ylamino]-pyridine-3-carbonyl}-amino)-pyrrolidine-1,2-dicarboxylic acid 1-tert-butyl ester A solution of ester, 4-({4-[2-(5-Chloro-2-fluoro-phenyl)-5-methoxy-pyrimidin-4-yl-amino]-pyridine-3-carbonyl}-amino)-pyrrolidine-1,2-dicarboxylic acid 1-tert-butyl ester 2-methyl ester (400 mg) in 1 M NaOH (1 mL) and dioxane (6 mL) was heated at 60° C. for 2.5 hours. 1 M HCl (2 mL) was added and the reaction mixture partitioned between water (50 mL) and CH$_2$Cl$_2$ (50 mL). The aqueous layer was further extracted with CH$_2$Cl$_2$ (3×50 mL) and the extracts were combined and the solvent was removed in vacuo. Purification by preparative HPLC (5/95 water/acetonitrile/ 20 mins) afforded 4-({4-[2-(5-chloro-2-fluoro-phenyl)-5-methoxy-pyrimidin-4-ylamino]-pyridine-3-carbonyl}-amino)-pyrrolidine-1,2-dicarboxylic acid 1-tert-butyl ester (110 mg, 0.187 mmol 28% yield).

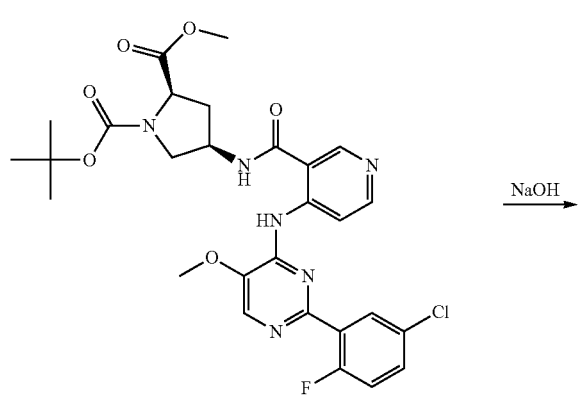

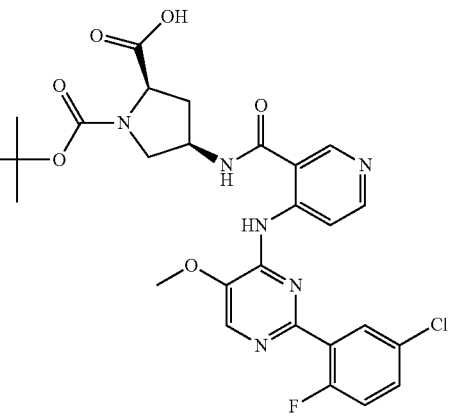

-continued

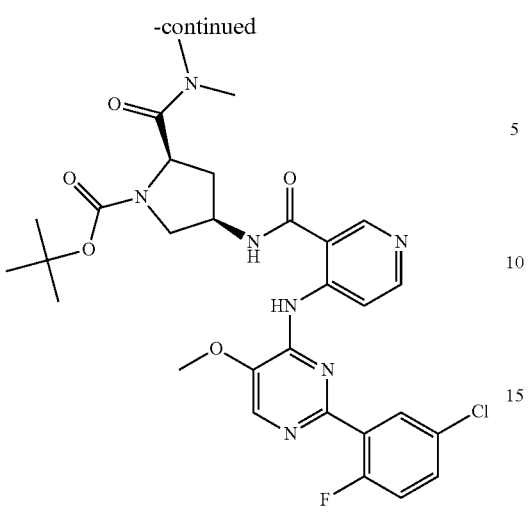

The dimethyl amide was formed from the carboxylic acid as described in Example 3 above.

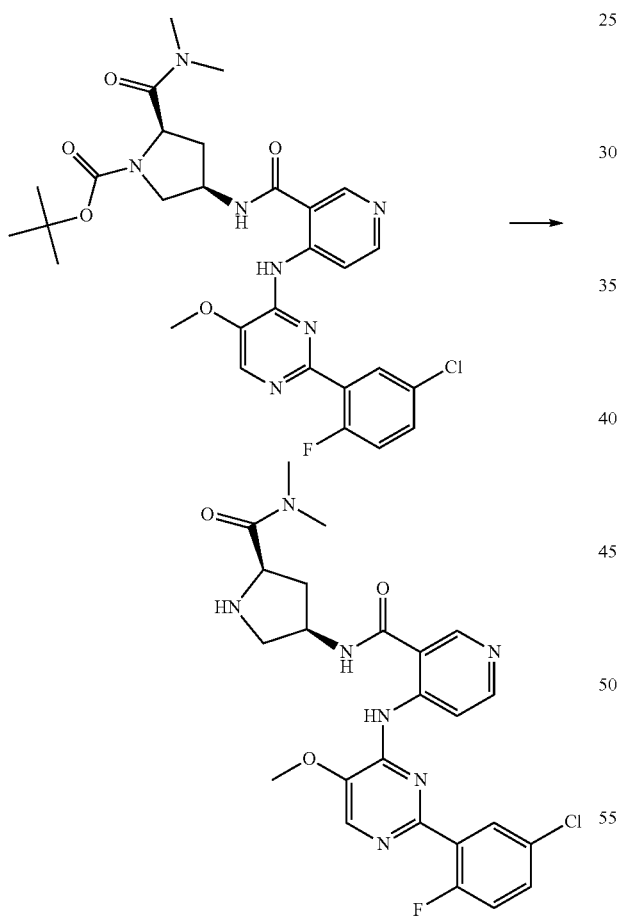

4-[2-(5-Chloro-2-fluoro-phenyl)-5-methoxy-pyrimidin-4-ylamino]-N-(5-dimethylcarbamoyl-pyrrolidin-3-yl)-nicotinamide The Boc-protected amine, 4-({4-[2-(5-chloro-2-fluoro-phenyl)-5-methoxy-pyrimidin-4-ylamino]-pyridine-3-carbonyl}-amino)-2-dimethylcarbamoyl-pyrrolidine-1-carboxylic acid tert-butyl ester (48 mg, 0.078 mmol) in 4 M HCL dioxane (2 mL) was stirred at room temperature for 3 hours. The solvent was removed in vacuo. Re-dissolved in DMF and purified by preparative HPLC (5/70 water/acetonitrile/ 20 mins) to afford 4-[2-(5-chloro-2-fluoro-phenyl)-5-methoxy-pyrimidin-4-ylamino]-N-(5-dimethylcarbamoyl-pyrrolidin-3-yl)-nicotinamide (26 mg, 0.051 mmol 65%).

Example 16

Preparation of a Pyridine N-Oxide Compound

Synthesis of 4-[2-(5-Chloro-2-fluoro-phenyl)-5-methoxy-pyrimidin-4-ylamino]-Ncyclopropyl-1-oxy-nicotinamide

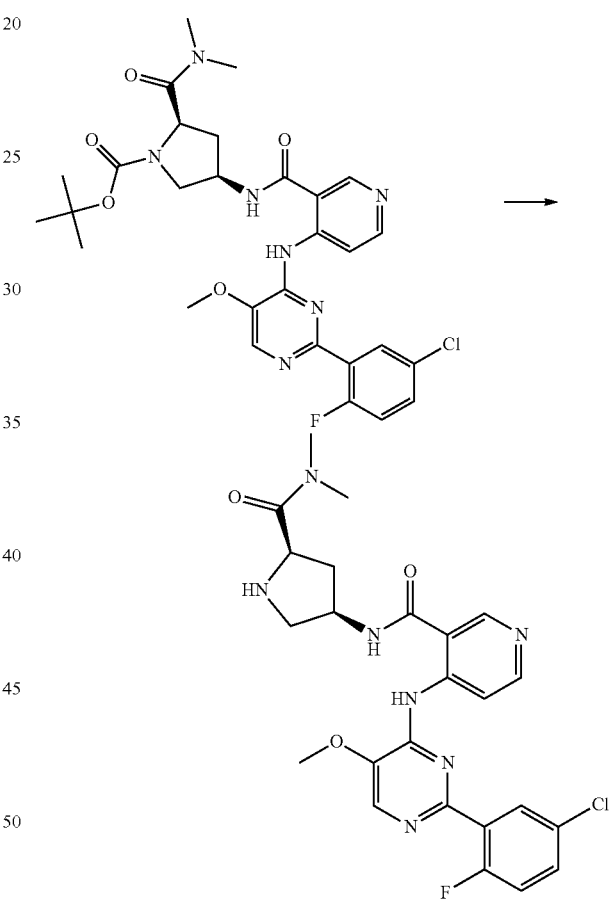

4-[2-(5-Chloro-2-fluoro-phenyl)-5-methoxy-pyrimidin-4-ylamino]-Ncyclopropyl-1-oxy-nicotinamide To a 350 mL round pressure vessel was added 4-[2-(5-chloro-2-fluoro-phenyl)-5-methoxy-pyrimidin-4-ylamino]-N-cyclopropyl-nicotinamide (1.28 g, 3.105 mmol) followed by methylene chloride (30 ml). The flask was placed in an ice-bath at 0° C. While maintaining the temperature at 0-2° C. mCPBA (2.15 g of 77%, ~9.6 mmol) was added and the reaction mixture was allowed to stir in the sealed reaction flask. After 2 hours the reaction was quenched by adding of saturated sodium bicarbonate (30 mls) and extracted with dichloromethane (2×50 ml). The organic layer, which contained suspended solid, was separated, filtered and washed with acetone (3×50 ml). The remaining bright yellow solid contained 4-[2-(5-chloro-2-fluoro-phenyl)-5-methoxy-pyrimidin-4-ylamino]-N-cyclopropyl-1-oxynicotinamide was purified by HPLC (yield=65.8%).

Example 17

Activity of Selected Compounds of the Invention

Replicon Assay.

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion ($neo^R$, neomycine phosphotransferase). The construct is bordered by 5' and 3' NTRs (non-translated regions) from HCV type 1b. Continued culture of the replicon cells in the presence of G418 ($neo^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. $EC_{50}$ values were then calculated, which value represents the amount of the compound required to decrease by 50% the level of detected luciferase activity, or more specifically, the ability of the genetically linked HCV replicon RNA to replicate.

The following Table 1 lists compounds that were tested for activity in the inhibition of HCV RNA replication in a cellular assay according to the procedure described above. Table 1 provides as well structure characterization data for the compounds of formula (I) as described herein. The compounds in Table 1 are characterized in part by their biological activity and in part by their structure: the compounds were characterized in part by LC-mass spectrometry, and the second column of the Table provides the observed parent ion that was observed in the LC-MS analysis of the compounds that were prepared by the methods described above. In each case, the expected parent ion was observed, and the Table further provides the LC conditions under which the mass spectrum was measured as well as the retention time of the observed product.

TABLE 1

| Nr. | Structure | m/z (M + H$^+$), HPLC retention time (min)* | EC$_{50}$ (µM) |
| --- | --- | --- | --- |
| 1 | 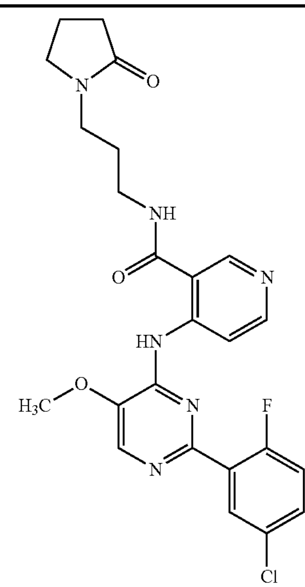 | 499.19, 2.78$^a$ | 0.08399 |

AutoNom Name:
4-[2-(5-Chloro-2-fluoro-phenyl)-5-methoxy-pyrimidin-4-ylamino]-N-[3-(2-oxo-pyrrolidin-1-yl)-propyl]-nicotinamide TABLE 1-continued

| Nr. | Structure | m/z (M + H⁺), HPLC retention time (min)* | EC$_{50}$ (μM) |
|---|---|---|---|
| 2 | Autonom Name: 4-[2-(5-Chloro-2-fluoro-phenyl)-5-methoxy-pyrimidin-4-ylamino]-N-(2,2,2-trifluoro-ethyl)-nicotinamide | 456.0, 1.393 | 1.160486 |
| 3 | Autonom Name: 4-[2-(5-Chloro-2-fluoro-phenyl)-5-methoxy-pyrimidin-4-ylamino]-N-tetrahydro-furan-2-ylmethyl)-nicotinamide (Chiral) | 458.1, 1.34 | 2.637242 |
| 4 | AutoNom Name: ({4-[2-(5-Chloro-2-fluoro-phenyl)-5-methoxy-pyrimidin-4-ylamino]-pyridine-3-carbonyl}-amino)-acetic acid ethyl ester | 460.1, 1.360 | 4.615407 |

TABLE 1-continued
| Nr. | Structure | m/z (M + H+), HPLC retention time (min)* | EC$_{50}$ (μM) |
|---|---|---|---|
| 5 | 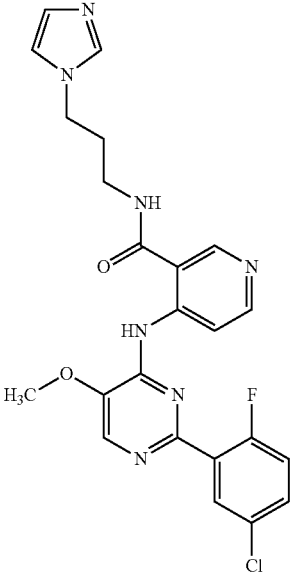<br>AutoNom Name:<br>4-[2-(5-Choro-2-fluoro-phenyl)-5-methoxy-pyrimidin-4-ylamino]-N-(3-imidazol-1-yl-propyl)-nicotinamide | 482.15, 2.36$^a$ | 0.921319 |
| 6 | 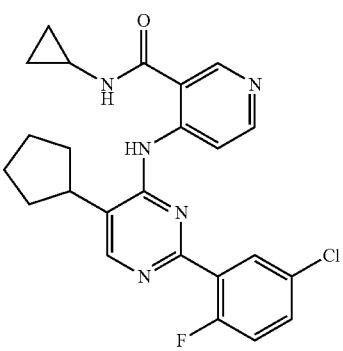<br>Autonom Name:<br>4-[2-(5-Chloro-2-fluoro-phenyl)-5-cyclopentyl-pyrimidin-4-ylamino]-N-cyclopropyl-nicotinamide | 452.4, 1.620 | 12.69931 |

TABLE 1-continued
| Nr. | Structure | m/z (M + H+), HPLC retention time (min)* | EC$_{50}$ (μM) |
|---|---|---|---|
| 7 | 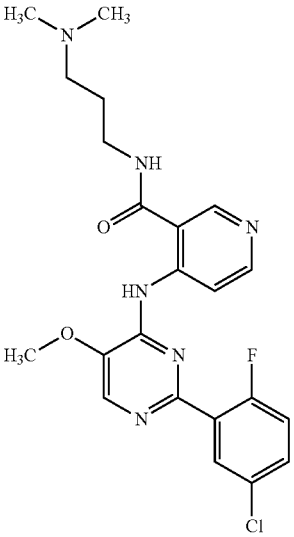 Autonom Name: 4-[2-(5-Chloro-2-fluoro-phenyl)-5-methoxy-pyrimidin-4-ylamino]-N-(3-dimethylamino-propyl)-nicotinamide | 415.29, 2.46$^a$ | 0.59547 |
| 8 | 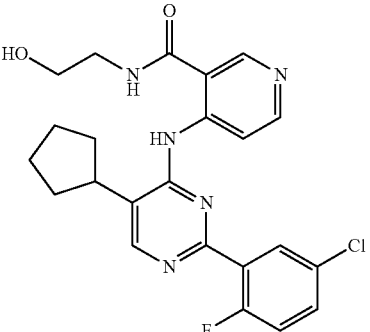 Autonom Name: 4-[2-(5-Chloro-2-fluoro-phenyl)-5-cyclopentyl-pyrimidin-4-ylamino]-N-(2-hydroxy-ethyl)-nicotinamide | 456.2, 1.467 | 16.37834 |

TABLE 1-continued
| Nr. | Structure | m/z (M + H$^+$), HPLC retention time (min)* | EC$_{50}$ (μM) |
|---|---|---|---|
| 9 | 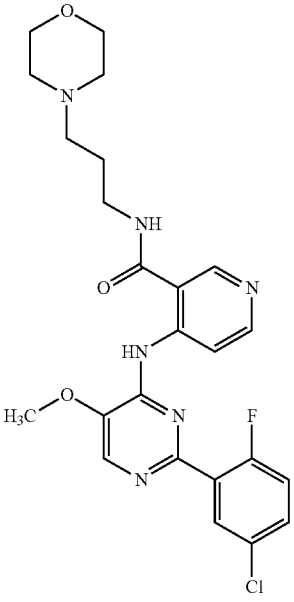 Autonom Name: 4-[2-(5-Chloro-2-fluoro-phenyl)-5-methoxy-pyrimidin-4-ylamino]-N-(3-morpholin-4-yl-propyl)-nicotinamide | 501.17, 2.36$^a$ | 1.100829 |
| 10 | 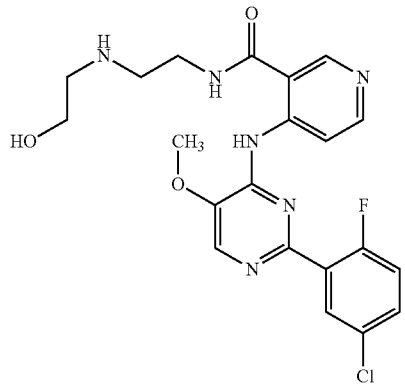 Autonom Name: 4-[2-(5-Chloro-2-fluoro-phenyl)-5-methoxy-pyrimidin-4-ylamino]-N-(2-(2-hydroxy-ethylamino)-ethyl]-nicotinamide | 461.1, 1.07 | 1.480744 |

TABLE 1-continued
| Nr. | Structure | m/z (M + H+), HPLC retention time (min)* | EC$_{50}$ (μM) |
|---|---|---|---|
| 11 | 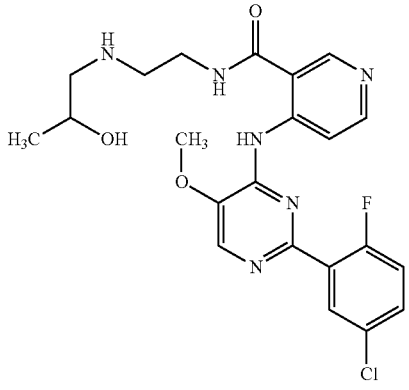<br>Autonom Name:<br>4-[2-(5-Chloro-2-fluoro-phenyl)-5-methoxy-pyrimidin-4-ylamino]-N-[2-(2-hydroxy-propylamino)-ethyl]-nicotinamide | 475.1, 1.11 | 1.143563 |
| 12 | 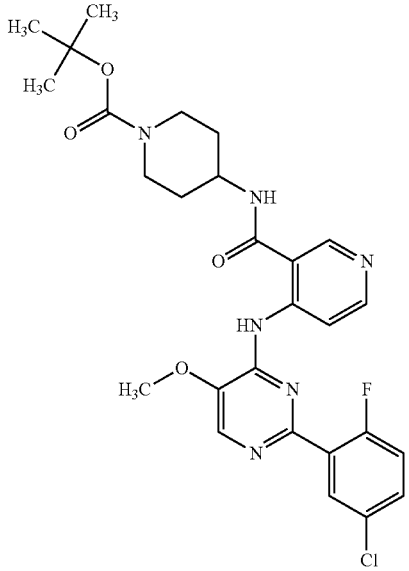<br>Autonom Name:<br>4-({4-[2-(5-Chloro-2-fluoro-phenyl)-5-methoxy-pyrimidin-4-ylamino]-pyridine-3-carbonyl}-amino)-piperidine-1-carboxylic acid tert-butyl ester | 457.16, 2.46$^a$ | 1.012931 |

TABLE 1-continued

| Nr. | Structure | m/z (M + H⁺), HPLC retention time (min)* | EC$_{50}$ (μM) |
|---|---|---|---|
| 13 | 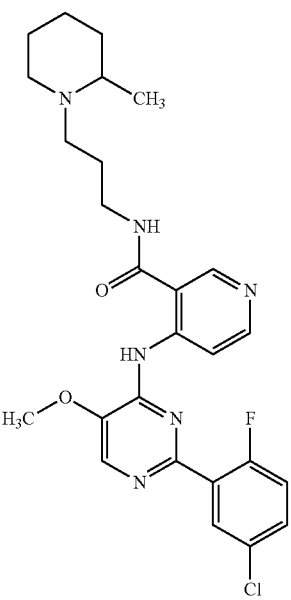 Autonom Name: 4-[2-(5-Chloro-2-fluoro-phenyl)-5-methoxy-pyrimidin-4-ylamino]-N-[3-(2-methyl-piperidin-1-yl)-propyl]-nicotinamide | 513.22, 2.51$^a$ | 0.550364 |
| 14 | 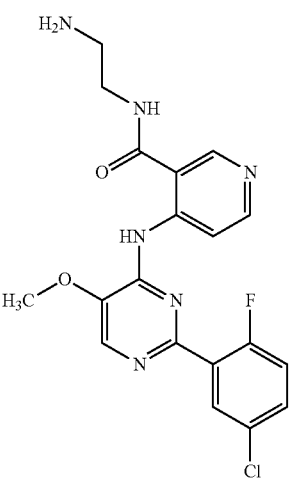 Autonom Name: N-(2-Amino-ethyl)-4-[2-(5-chloro-2-fluoro-phenyl)-5-methoxy-pyrimidin-4-ylamino]-nicotinamide | 417.0, 1.10 | 3.670118 |

HPLC conditions: HPLC Column: Merck AGA Chromolith Flash column (25 × 4.6 mm)

HPLC solvents:

A: water with 0.1% trifluroacetic acid.

B: acetonitrile with 0.1% trifluoroacetic acid.

Standard Gradient: 5% B to 95% B over 2.5 minutes with a flow rate of 3.0 mL/min.

$^a$Alternative Gradient: 5% B to 95% B over 4 minutes at a flow rate of 3.0 mL/min.

The invention claimed is:
1. A method for diminishing hepatitis C virus (HCV) viral load in a patient infected with hepatitis C virus comprising administering to the patient an amount of a compound of formula (I) effective to diminish the HCV viral load in the patient:

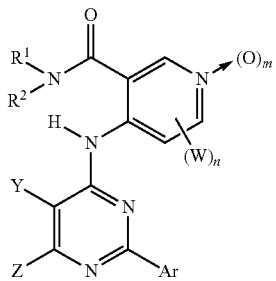

wherein Ar is an optionally substituted phenyl ring;
Y is H, halo, NO$_2$, or an optionally substituted member selected from the group consisting of alkyl, cycloalkyl, alkenyl, alkynyl, heteroalkyl, heteroalkenyl, heteroalkynyl, aryl, heteroaryl, arylalkyl, heteroarylalkyl, acyl, and heteroacyl,
  or Y can be NR$_2$, wherein each R is independently H or an optionally substituted alkyl, cycloalkyl, alkenyl, alkynyl, acyl, aryl, or arylalkyl group or a heteroform of any of these groups, and wherein two R groups can cyclize to form an optionally substituted 3-8 membered heterocyclic ring;
R$^1$ represents an optionally substituted group that is alkyl, cycloalkyl, heteroalkyl, acyl, alkoxy, alkylamino, heteroacyl, aryl, heteroaryl, arylalkyl, or heteroarylalkyl, wherein each heteroalkyl, heteroacyl, heteroaryl, and heteroarylalkyl includes one or more heteroatoms that is O, N, S, or P,
  provided that R$^1$ is not a group of the formula —CH$_2$—CH(OH)—R$^4$, wherein R$^4$ is H or an optionally substituted hydrocarbyl group that does not comprise an amine;
R$^2$ is H, or R$^2$ is CH$_2$ and R$^1$ and R$^2$ cyclize to form an optionally substituted piperidinyl, morpholinyl, or piperazinyl ring, or a pyrrolidinyl ring substituted with at least one amino or halo substituent;
Z is H, halo, NO$_2$, or an optionally substituted member that is alkyl, cycloalkyl, alkenyl, alkynyl, heteroalkyl, heteroalkenyl, heteroalkynyl, aryl, heteroaryl, arylalkyl, heteroarylalkyl, acyl, or heteroacyl, or Z is NR$^2$,
  wherein each R is independently H or an optionally substituted alkyl, cycloalkyl, alkenyl, alkynyl, acyl, heteroacyl, aryl or arylalkyl group or a heteroform of any of these groups;
each W is independently halo, NR$_2$, NO$_2$, CN, CF$_3$, or an optionally substituted member that is alkyl, cycloalkyl, alkenyl, alkynyl, heteroalkyl, heteroalkenyl, heteroalkynyl, aryl, heteroaryl, acyl, heteroacyl, arylalkyl, or heteroarylalkyl,
  wherein each R is independently H or an optionally substituted alkyl, cycloalkyl, alkenyl, alkynyl, acyl, aryl, heteroalkyl or heteroaryl group;
m is 0 or 1;
n is 0-3;
and
  (a) Y is a 5-6 membered cyclic amine, OH, F, Cl, Br, or I; or
  (b) m is 1; or
  (c) R$^1$ is OH or an optionally substituted alkoxy r an optionally substituted alkylamine, or
  (d) R$^2$ is CH$_2$ and R$^1$ and R$^2$ cyclize to form an optionally substituted piperidine, morpholine, or piperazine ring, or a pyrrolidine ring substituted with at least one amino or halo substituent;
  (e) R$^1$ is C—NH$_2$, a nitrile, a lactam or a lactone ring, or a ketone, or an optionally substituted 4-5 membered cyclic amine; or
  (f) R$^1$ is comprises at least two substructures independently selected from the group consisting of:
    (1) C—NH—C,
    (2) C—OH,
    (3) C=O,
    (4) P=O,
    (5) S=O,
    (6) C=N,
    (7) a non-cyclic ether oxygen,
    (8) a tertiary non-acylated amine;
    (9) a 5-6 membered aromatic or heteroaromatic ring,
    (10) C—X where X is OH, Cl, or F,
    (11) C$_T$—O—R$^4$, wherein C$_T$ is a carbon bonded to three other carbon atoms, and R$^4$ is H or an optionally substituted hydrocarbyl group, and
    (12) an optionally substituted 3 to 8 membered carbocyclic ring; or
  (g) R$^1$ is —(CH$_2$)$_3$—OR$_4$ or —(CH$_2$)$_2$—N(R$_4$)$_2$, wherein each R$^4$ is independently H or an optionally substituted hydrocarbyl group;
or a pharmaceutically acceptable salt thereof.
2. The method according to claim 1, wherein Ar is a substituted phenyl.
3. The method according to claim 1, wherein Ar is substituted with 1-2 groups that are halo, C1-C4 alkyl, CN, CF$_3$, or C1-C4 alkoxy.
4. The method according to claim 1 wherein n is 0 or 1.
5. The method according to claim 1, wherein Z is H.
6. The method according to claim 5, wherein Y is halo, OH, OR, NR$_2$, or R, wherein each R is an optionally substituted that is C1-C8 alkyl, C1-C8 heteroalkyl, C6-C12 arylalkyl, or C6-C12 heteroarylalkyl, and where two R groups of NR$_2$ can optionally cyclize to form a 3-8 membered ring containing 1-2 heteroatoms that are N, O, or S.
7. The method according to claim 5, wherein Y is 1-pyrrollidinyl, cyclopentyl, F, Cl, Br, I, or OH.
8. The method according to claim 1, wherein R$^1$ is at least one S=O or P=O.

9. The method according to claim 1, wherein $R^1$ is at least one C—NH—C or C—OH.

10. The method according to claim 1, wherein $R^1$ is at least one C=N or C≡N.

11. The method according to claim 1, wherein $R^1$ is at least one C—F or one C—Cl or one tertiary alcohol.

12. The method according to claim 1, wherein $R^1$ is at least one cyclic ether or C=O.

13. The method according to claim 1, wherein $R^1$ is at least one aryl, heteroaryl, lactam, or lactone ring.

14. The method according to claim 8, wherein Z is H.

15. The method according to claim 14, wherein Ar is phenyl substituted with 1-2 groups selected from halo, CN, $CF_3$, C1-C4 alkyl, or C1-C4 alkoxy.

16. The method according to claim 15, wherein n is 0 or 1, and W if present is halo, methyl, $CF_3$, or OMe.

17. The method according to claim 14, wherein Y is halo, C1-C5 alkyl, OH, OR, or $NR_2$, wherein each R is an optionally substituted group that is independently C1-C8 alkyl, C1-C8 heteroalkyl, or C6-C10 arylalkyl, and wherein two R groups of $NR_2$ can cyclize to form a 3-8 membered optionally substituted heterocyclic ring containing 1-2 heteroatoms that are N, O, or S.

18. The method according to claim 15, wherein n is 0.

19. The method according to claim 18, wherein Ar is phenyl substituted with at least one F, Cl or Br.

20. The method according to claim 18, wherein Ar is substituted with at least two halo substituents.

21. The method according to claim 1, wherein m is 1.

22. The method according to claim 1, wherein m is 0.

23. The method according to claim 1, wherein the compound has the formula (II):

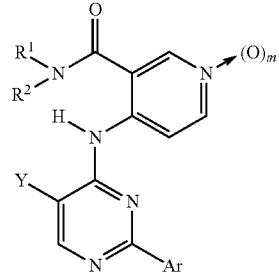

(II)

and the salts thereof, wherein
Ar is a phenyl optionally substituted with one or two halo.

24. The method of claim 1, wherein the viral load of the patient is diminished to an undetectable level.

25. The method of claim 1, further comprising administering to the patient another anti-HCV compound.

26. The method of claim 25, wherein the other anti-HCV compound is interferon-α, pegylated interferon-α, ribavirin, or a combination thereof.

27. The method of claim 25, wherein the other anti-HCV compound is an HCV polymerase inhibitor, and HCV protease inhibitor, helicase, a metalloprotease inhibitor, an immunomodulatory agent, ribavirin, amantadine, telbivudine, an IMPDH inhibitor, or a combination thereof.

* * * * *